United States Patent
Suh et al.

(10) Patent No.: US 11,235,311 B2
(45) Date of Patent: Feb. 1, 2022

(54) CATALYST FOR PRODUCING ALIPHATIC KETONES FROM FERMENTED PRODUCT OF BIOMASS, AND METHOD FOR PRODUCING SAME

(71) Applicant: INDUSTRY-UNIVERSITY COOPERATION FOUNDATION HANYANG UNIVERSITY, Seoul (KR)

(72) Inventors: Young Woong Suh, Seoul (KR); Min Seok Kim, Seoul (KR); Jong Ha Park, Seoul (KR)

(73) Assignee: INDUSTRY-UNIVERSITY COOPERATION FOUNDATION HANYANG UNIVERSITY, Seoul (KR)

( * ) Notice: Subject to any disclaimer, the term of this patent is extended or adjusted under 35 U.S.C. 154(b) by 98 days.

(21) Appl. No.: 16/477,419

(22) PCT Filed: Jan. 9, 2018

(86) PCT No.: PCT/KR2018/000397
§ 371 (c)(1),
(2) Date: Jul. 11, 2019

(87) PCT Pub. No.: WO2018/131865
PCT Pub. Date: Jul. 19, 2018

(65) Prior Publication Data
US 2019/0358611 A1    Nov. 28, 2019

(30) Foreign Application Priority Data

Jan. 11, 2017    (KR) .................. 10-2017-0003995

(51) Int. Cl.
*B01J 23/72*    (2006.01)
*B01J 35/00*    (2006.01)
(Continued)

(52) U.S. Cl.
CPC ........... *B01J 23/72* (2013.01); *B01J 35/0053* (2013.01); *B01J 35/1014* (2013.01);
(Continued)

(58) Field of Classification Search
CPC .... B01J 23/72; B01J 35/0053; B01J 35/1014; B01J 37/0018; B01J 37/0207; B01J 37/03; B01J 37/16; C07C 45/45; C12P 7/36

See application file for complete search history.

(56) References Cited

U.S. PATENT DOCUMENTS 5,904,913 A * 5/1999 Bohm ................. C01B 3/326
                                                    423/648.1
2005/0250966 A1* 11/2005 Funakoshi ............ C07C 17/266
                                                    570/172
(Continued)

FOREIGN PATENT DOCUMENTS

CN        105308015 A    2/2016
JP        2005-131468 A  5/2005
(Continued)

OTHER PUBLICATIONS

Zhang et al. ("Comparative Study on Catalytic Properties for Low-Temperature CO Oxidation of Cu/CeO2 and CuO/CeO2 Prepared via Solvated Metal Atom Impregnation and Conventional Impregnation", Catalysis Letters 80, (2002) 41-46). (Year: 2002).*
(Continued)

*Primary Examiner* — Sheng H Davis
*Assistant Examiner* — Michael Forrest
(74) *Attorney, Agent, or Firm* — Sughrue Miom, PLLC

(57) ABSTRACT

The present disclosure discloses: a bifunctional Cu/Ce—Zr-based catalyst suitable for reacting a ketone and alcohol which are contained in a fermented product of biomass and have a low molecular weight, and converting same into an
(Continued)

aliphatic ketone having an increased carbon number; a method for producing the catalyst; and a method for producing a fuel-range aliphatic ketone, such as gasoline and air fuel, by using the catalyst.

18 Claims, 14 Drawing Sheets

(51) Int. Cl.
| | |
|---|---|
| B01J 35/10 | (2006.01) |
| B01J 37/00 | (2006.01) |
| B01J 37/02 | (2006.01) |
| B01J 37/03 | (2006.01) |
| B01J 37/16 | (2006.01) |
| C07C 45/45 | (2006.01) |
| C12P 7/36 | (2006.01) |

(52) U.S. Cl.
CPC ....... *B01J 37/0018* (2013.01); *B01J 37/0207* (2013.01); *B01J 37/03* (2013.01); *B01J 37/16* (2013.01); *C07C 45/45* (2013.01); *C12P 7/36* (2013.01)

(56) References Cited

U.S. PATENT DOCUMENTS

| | | | |
|---|---|---|---|
| 2014/0137465 A1 | 5/2014 | Toste et al. | |
| 2016/0152907 A1* | 6/2016 | Baer | C10L 1/02 |
| | | | 435/148 |

FOREIGN PATENT DOCUMENTS

| | | |
|---|---|---|
| JP | 2014-518629 A | 8/2014 |
| KR | 10-2009-0041202 A | 4/2009 |
| KR | 10-1533541 B1 | 7/2015 |
| TW | 200711738 A | 4/2007 |

OTHER PUBLICATIONS

Gangadharan et al ("Condensation reactions of propanal over CexZr1-xO2 mixed oxide catalysts", Appl Cata A: General 385 (2010) 80-91). (Year: 2010).*
Gimenez-Manogil et al (Preparation, characterization and testing of CuO/Ce0.8Zr0.2O2 catalysts for NO oxidation to NO2 and mild temperature diesel soot combustion, Appl. Cata. B: Environ. 152-153 (2014) 99-107). (Year: 2014).*
Pokrovski et al. ("An investigation of the factors influencing the activity of Cu/CexZr1-xO2 for methanol synthesis via CO hydrogenation" J Cata. 241 (2006) 276-286) (Year: 2006).*
Kaminski et al ("Mesoporous cerium-zirconium oxides modified with gold and copper—synthesis, characterization and performance in selective oxidation of glycerol" RSC Adv., 2017, 7, 7801-7819) (Year: 2017).*
Shu-Ping Wang, et al., "Comparison of $CuO/Ce_{0.8}Zr_{0.2}O_2$ and $CuO/CeO_2$ catalysts for low-temperature CO oxidation", Catalysis Letters, Dec. 2005, pp. 163-168, vol. 105, Nos. 3-4.
KR Office Action for Application No. 10-2017-0003995 dated Mar. 19, 2018.
KR Notice of Allowance Application No. 10-2017-0003995 dated Oct. 15, 2018.
KR Certificate of Patent for Application No. 10-2017-0003995 dated Nov. 12, 2018.
International Search Report for PCT/KR2018/000397 dated Apr. 16, 2018 [PCT/ISA/210].
Communication dated Sep. 18, 2021 from the China National Intellectual Property Administration in CN Application No. 201880006588.8.

* cited by examiner

CATALYST FOR PRODUCING ALIPHATIC KETONES FROM FERMENTED PRODUCT OF BIOMASS, AND METHOD FOR PRODUCING SAME

CROSS REFERENCE TO RELATED APPLICATIONS

This application is a National Stage of International Application No. PCT/KR2018/000397, filed on Jan. 9, 2018, which claims priority from Korean Patent Application No. 10-2017-0003995, filed on Jan. 11, 2017.

TECHNICAL FIELD

The present disclosure relates to a catalyst for producing aliphatic ketones from a fermented product of biomass and a method for producing same. More specifically, the present disclosure relates to a bifunctional Cu/Ce—Zr-based catalyst, which is suitable for converting a low-molecular weight ketone and an alcohol contained in a fermented product of biomass into aliphatic ketones having increased carbon atoms, to a method for producing the catalyst, and to a method for producing fuel-range aliphatic ketones, such as gasoline and jet oil, by using the catalyst.

BACKGROUND ART

Petroleum energy leaded human development, but it has problems, such as resource finitude, mal-distribution and environmental pollution. Accordingly, research about the entire/partial replacement petroleum resources with biomass is actively being carried out.

The term biomass is used to broadly refer to any material of biological origin and narrowly refer to materials derived from mainly plant sources, such as corn, soybeans, linseed, sugarcane, and palm oil. However, the term biomass may extend to all living organisms, or metabolic byproducts, which account for a part of the carbon cycle.

Research on the production of high-value-added materials from biomass has been actively carried out since the 1970s. For example, carbohydrates in biomass are converted into fermentable sugars capable of ethanol fermentation, from which oxygen-containing compounds (e.g., ethanol, butanol, organic acid, acetone, etc.) can be produced. Most of the compounds converted from biomass through such a fermentation process are oxygen-containing compounds (oxygenates) having a low number of carbon atoms, and in order to apply such compounds to fuel oil such as gasoline, subsequent reaction processes, such as ketonization and condensation, are required. Especially, acetone contained in fermented products of biomass is one of the lowest value added compounds, and is produced together in the production of bioethanol and/or biobutanol. Therefore, techniques to produce high-value-added compounds using low-value-added acetone have been studied.

An exemplary reaction route has been recently proposed that acetone, ethanol, and butanol produced via anaerobic fermentation are converted into hydrocarbons of jet fuel range. The most important step in this conversion is an aldol condensation reaction between acetone and an alcohol, resulting in mono- and di-branched aliphatic ketones. For example, 2-heptanone (C7 ketone; 1:1 on a molar ratio basis) and 6-undecanone (C11 ketone; 1:2 on a molar ratio basis) are produced by a reaction of acetone (C3 ketone) and butanol (C4 alcohol). Since the efficiency of this step determines the total yield of hydrocarbons, a highly active cross-aldol condensation reaction catalyst is required.

This type of reaction requires two catalytic functions, specifically metal sites for alcohol dehydrogenation and base sites for condensation. According to the recent research, a technique in which a noble metal-supported catalyst and $K_3PO_4$ are used together has been known, and it has been reported that catalysts in which Pd, Ru, and Cu are loaded on MgO—$Al_2O_3$ hydrotalcite support show high catalytic performance. A technique in which acetone and furfural are formed into a long-chain hydrocarbon via condensation in the presence of a catalyst in which Pt or Pd is loaded on MgO—$ZrO_2$ support is known. These mixed oxide supports can not only provide optimum basicity required for a reaction since MgO shows a tendency of self-aldol condensation of acetone, but also improve the dispersion of loaded metal particles due to a large specific surface area resulting from the mixing of two kinds of metal oxides.

A catalyst system composed of an optimum active metal (Pd) and an optimum homogeneous basic catalyst ($K_3PO_4$) on the basis of reaction conditions (optimum temperature, optimum time, kind of solvent, ratio of metal catalyst and basic catalyst, etc.) has also been recently developed, wherein in order to increase the palladium (Pd) dispersion, carbon (C) with a high surface area is used as a support and various Pd precursors are used, and this corresponds to a technique in which Pd is focused as a supported metal (US Patent Publication NO. 2014/0137465, etc.).

In order to obtain an aldehyde reacting with acetone via aldol condensation, a catalyst in which low-priced copper (Cu) as a metal to convert an alcohol in a fermented product is loaded on a support, such as hydrotalcite (HT), which is a heterogeneous basic catalyst component, is also known (US Patent Publication NO. 2016/0152907). According to such technique, for enhancement of base sites, a heterogeneous basic catalyst (an alkali metal, an alkali earth metal, a lanthanide metal, etc.) is further added to improve activity. However, copper (Cu) is present in an unstable state in a supported catalyst and thus is not strongly deposited on the support, and therefore the leaching of copper (Cu) occurs during reactions, and as a result, the durability of the catalyst deteriorates. This leaching also occurs when ceria ($CeO_2$) or zirconia ($ZrO_2$) besides hydrotalcite is used as a support.

Furthermore, desired catalytic activity inherent to copper is difficult to obtain, for example, copper particles loaded on the support are not homogeneously dispersed. Moreover, in order to increase the yield of aliphatic ketones as much as possible from acetone and alcohol compounds in fermented products of biomass, the amount of base sites in the catalyst support, necessary for aldol condensation, needs to be properly adjusted.

However, it is difficult to control the dispersion of copper and the amount of base sites while suppressing the deterioration of durability of a copper-based support catalyst.

DETAILED DESCRIPTION OF THE INVENTION

Technical Problem

Therefore, an embodiment of the present disclosure is to provide: a Cu/Ce—Zr-based catalyst, among copper-based supported catalysts, capable of suppressing the deterioration of durability due to the leaching of copper during a reaction and controlling the dispersion of copper and the amount of base sites in a support; and a method for producing the Cu/Ce—Zr-based catalyst.

Furthermore, another embodiment of the present disclosure is to provide a method for producing aliphatic ketones, especially aliphatic ketones of fuel range, at high yields, from a ketone (e.g., acetone) with low molecular weights and an alcohol (e.g., butanol) in a microbial fermentation product of biomass in the presence of a Cu/Ce—Zr-based catalyst having improved catalytic activity.

Technical Solution

In accordance with a first aspect of the present disclosure, there is provided a method for producing a Cu/Ce—Zr-based catalyst, the method including:
a) preparing a mixed support represented by a general formula $Ce_xZr_{1-x}O_2$ (x is 0.5-0.95);
b) loading a $Cu^{2+}$ precursor on the mixed support; and
c) converting the $Cu^{2+}$ precursor-loaded mixed support into its oxide form via calcination,
wherein (i) the Cu content is 0.5-20 wt % on the element basis, (ii) the oxygen storage capacity is 500-1000 μmol/g, and (iii) the specific Cu surface area is 1-60 m$^2$/g.

According to an exemplary embodiment, the specific (BET) surface area of the mixed support prepared in step a) may be at least 90 m$^2$/g and the specific (BET) surface area of the oxide prepared in step c) is at least 70 m$^2$/g.

According to an exemplary embodiment, the $Cu^{2+}$ precursor, as a water-soluble copper salt, may be copper nitrate, copper sulfate, copper acetate, copper formate, copper (II) chloride, copper iodide, or a combination thereof.

According to an exemplary embodiment, step a) may include:
a1) preparing precursor solutions for a support, the precursor solutions containing a Ce precursor and a Zr precursor;
a2) forming a Ce—Zr composite precursor from the precursor solutions for a support; and
a3) calcining the Ce—Zr composite precursor to form a mixed support in an oxide form.

According to an exemplary embodiment, step b) may be performed by impregnation.

In accordance with a second aspect of the present disclosure, there is provided a Cu/Ce—Zr-based catalyst in which Cu particles are supported on a mixed support represented by $Ce_xZr_{1-x}O_2$ (x is 0.5-0.95),
wherein (i) the Cu content is 0.5 to 20 wt % on the element basis, (ii) the oxygen storage capacity is 500 to 1000 μmol/g, and (iii) the specific Cu surface area is 1 to 60 m$^2$/g.

According to an exemplary embodiment, the catalyst may have a form in which Cu particles or clusters are dispersed on the $Ce_xZr_{1-x}O_2$ mixed support and the size of the Cu particles or clusters may be in a rage of 5-100 nm.

According to an exemplary embodiment, the amount of $CO_2$-TPD in the catalyst may be in a range of 50-600 μmol/g.

In accordance with a third aspect of the present disclosure, there is provided a method for producing aliphatic ketones from a fermented product of biomass, the method including:
A) obtaining a fermented product of biomass containing acetone and butanol;
B) converting a reactant derived from the fermented product of biomass into aliphatic ketones via a condensation reaction using a Cu/Ce—Zr-based catalyst; and
C) separating and recovering the aliphatic ketones from the reaction product,
wherein in the Cu/Ce—Zr-based catalyst, Cu particles are supported on a mixed support represented by $Ce_xZr_{1-x}O_2$ (x is 0.5-0.95), and the Cu/Ce—Zr-based catalyst satisfies the following requirements (i) to (iii):
wherein (i) the Cu content is 0.5-20 wt % on the element basis, (ii) the oxygen storage capacity is 500-1000 μmol/g, and (iii) the specific Cu surface area is 1-60 m$^2$/g.

According to an exemplary embodiment, the method may further include, separating a reactant including acetone and butanol from the fermented product of biomass or separating a reactant including acetone, butanol, and ethanol from the fermented product of biomass, wherein the separated reactant may be provided as the reactant derived from the fermented product of biomass in step B).

According to an exemplary embodiment, the molar ratio of acetone:butanol in the separated reactant may be in a range of 0.1 to 2:1.

According to an exemplary embodiment, the molar ratio of acetone:butanol:ethanol in the separated reactant may be in a range of 0.1 to 10:2 to 10:1.

According to an exemplary embodiment, step B) may be performed under conditions of a temperature of 160 to 300° C. and a pressure of 1 to 100 bar.

According to an exemplary embodiment, the aliphatic ketones may have 6 to 14 carbon atoms.

According to an exemplary embodiment, the step of separating and recovering the aliphatic ketones from the reaction product may be performed by fractional distillation.

Advantageous Effects

In the Cu/Ce—Zr catalysts according to embodiments of the present disclosure, low-priced Cu but not conventional noble metal components is used as a metal component, and copper can be stably supported on a mixed support composed of oxides of Ce and Zr, without the leaching of a copper component through a strong interaction between the mixed support and the copper component. In addition, Cu can be uniformly dispersed in the mixed support by using oxygen vacancies in the mixed support, and the amount of base sites in the catalysts can be adjusted. Therefore, the Cu/Ce—Zr catalysts are effective in converting butanol and acetone in a fermented product of biomass into aliphatic ketones, especially fuel-range aliphatic ketones. Furthermore, the Cu/Ce—Zr catalysts can be produced by a relatively simple method even without an excessive change to a conventional catalyst production method. As a result, the Cu/Ce—Zr catalysts are expected to be widely commercialized in the future.

BEST MODE FOR CARRYING OUT THE INVENTION

Figure 1:
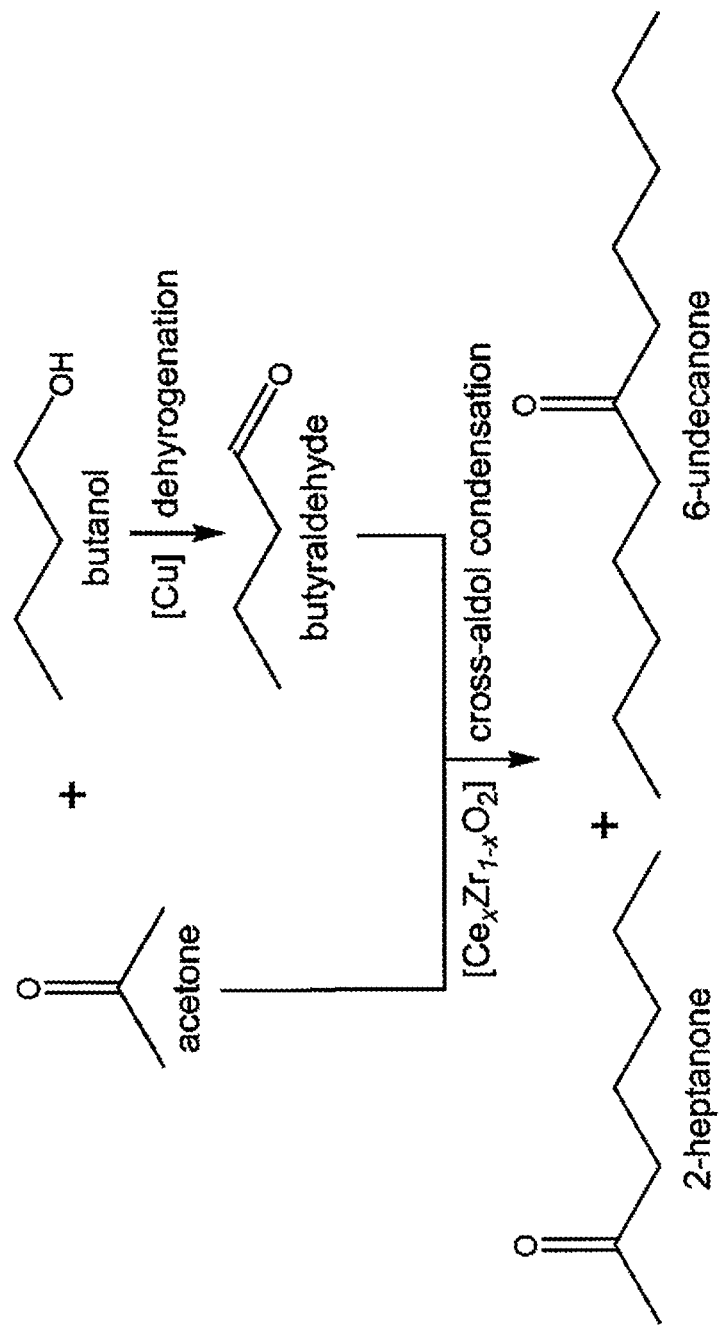
FIG. 1 schematically shows a reaction mechanism in which acetone and butanol in a fermented product of biomass are converted into aliphatic ketones in the presence of a Cu/Ce—Zr-based catalyst according to an embodiment of the present disclosure.

The present invention can be all accomplished by the following description. It is to be understood that the following description illustrates preferable embodiments of the present invention, but the present invention is not necessarily limited thereto. It is also to be understood that the accompanying drawings are included to provide a further understanding of the present invention and are not intended to limit the scope of the present invention.

The terms used herein may be defined as follows.

The term "biomass" generally refers to an organic matter produced by photosynthesis, but may be understood to encompass organic wastes, such as livestock muck and food waste. Broadly, the biomass may include plant biomass, specifically various biological resources known in the art, including cellulose, hemicellulose, and/or lignin (i.e., lignocellulose) (e.g., plant sources, such as corn, soybean, linseed, sugar cane, and palm oil, and more specifically, rice straw, wheat straw, starch-containing grains, corncob, cornstalk, rice husk, paper products, lumber, sawdust, agricultural wastes, grass, sugar cane, cotton, linen, bamboo, Manila hemp, algae, fruit peels, seaweed, palm wastes, and stems, roots, and leaves of plants, etc.). More specifically, the biomass may include carbohydrates obtained by saccharification or decomposition from the above-mentioned biomass, for example, starch and sugars, specifically monosaccharides (glucose, fructose, galactose, xylose, arabinose, mannose, etc.), disaccharides (sucrose, lactose, maltose, cellobiose, etc.), other (oligo)saccharides, and the like.

The term "crystalline" may typically refer to any solid material in which atoms are arranged to have a lattice structure (e.g., a three-dimensional order), and thus may be identified by X-ray diffraction (XRD), nuclear magnetic resonance (NMR), differential scanning calorimetry (DSC), or a combination thereof.

The term "oxygen vacancy" may refer to having the vacancy of an oxygen atom in a material structure, for example a non-stoichiometric oxide form.

The term "fermentation" may broadly refer to the decomposition of organic matter by microorganisms, and narrowly refer to an anaerobic organic matter decomposition process. There are ethanol fermentation by yeast and bacteria, acetone and butanol fermentation by the genus *Clostridium*, lactic fermentation by lactic acid bacteria, methane fermentation, hydrogen fermentation, and the like, according to the product. There is acetic fermentation as oxidative fermentation.

The term "reactant derived from fermented product of biomass" may refer to that treated to remove strains and the like contained in a fermented product, and more specifically refer to that additionally treated to have a composition suitable for a reactant in a subsequent reaction by separating some of moisture and carbon-containing compounds contained in the fermented product.

The term "aldol condensation reaction" may refer to a C—C coupling reaction, which occurs between two carbonyl compounds having a reactive alpha-hydrogen in at least one of carbonyl groups, and the aldol condensation reaction is typically used in coupling two ketone/aldehyde molecules to form a higher-molecular weight molecule, in which an acidic catalyst or a basic catalyst may be used.

FIG. 1 schematically shows a reaction mechanism in which acetone and butanol in a fermented product of biomass are converted into aliphatic ketones in the presence of a Cu/Ce—Zr-based catalyst according to an exemplary embodiment of the present disclosure.

The Cu/Ce—Zr-based catalyst is a bifunctional catalyst, wherein Cu provides a function of converting the butanol contained in the fermented product into butyl aldehyde via dehydration, while a Ce$_x$Zr$_{1-x}$O$_2$ support provides a function of forming aliphatic ketones having an increased number of carbon atoms via an aldol condensation reaction, specifically a cross-aldol condensation reaction between acetone and the converted butyl aldehyde. Here, the produced aliphatic ketones may be aliphatic ketones having 6 to 14 carbon atoms, specifically 7 to 11 carbon atoms, and may be 2-heptanon, 6-undecanon, and the like. The produced aliphatic ketones may correspond to a carbon range of fuel oil, especially, gasoline and jet fuel.

Catalyst Production

According to an embodiment, a Cu/Ce—Zr-based catalyst is a heterogeneous catalyst, and has a form in which Cu is supported on a mixed support represented by the general formula Ce$_x$Zr$_{1-x}$O$_2$ (x is 0.5-0.95, specifically 0.7-0.9, and more specifically 0.8-0.85). As such, the mixed support is in a form of a Ce and Zr composite oxide, and is rich in Ce. As a result, more Ce$^{3+}$ is present on the ceria-rich Ce$_x$Zr$_{1-x}$O$_2$ support, causing oxygen vacancies in its oxide surface.

For this, the mixed support may be prepared as an initial step. A Ce precursor (Ce$^{3+}$ or Ce$^{4+}$ precursor) and a Zr precursor (Zr$^{4+}$ precursor) may be used. As the precursors, metal salts, specifically, water-soluble metal salts may be used. Examples of the metal precursors may include halides (specifically chlorides), hydroxides, nitrates, sulfates, oxalates, carbonates, acetates, ammonium nitrate, phosphates, compounds containing oxides of the metal elements thereof (for example, oxynitrates), and may include one or a combination of two or more thereof. Also, the precursors may be in a form of mixed precursors of Ce and Zr, and thus may be, for example, a Ce/Zr mixed hydroxide.

According to an exemplary embodiment, the mixed support may be prepared by using a method known in the art, such as coprecipitation, hydrothermal synthesis, or decomposition, and specifically, coprecipitation, and more specifically, aqueous solution coprecipitation, organic solvent coprecipitation, or spray coprecipitation.

For example, the coprecipitation may be an aqueous solution coprecipitation, wherein a basic solution, specifically, a basic aqueous solution may be used as a precipitator. Here, hydroxides, such as ammonia and an alkali (e.g., sodium hydroxide, potassium hydroxide, ammonium hydroxide, etc.), carbonates (e.g., sodium carbonate, potassium carbonate, ammonium carbonate, etc.), or bicarbonates (e.g., sodium bicarbonate, ammonium bicarbonate, etc.) may be used as a basic component. The concentration of the basic solution (aqueous solution) is not particularly limited, but may be in a range of for example, about 0.1 to 4 M, specifically about 0.2 to 2 M, and more specifically about 0.3 to 1 M.

The amount of the precipitator is adjustable in the range required for the Ce precursor and the Zr precursor each to precipitate as hydroxides (e.g., $Ce(OH)_4$ and $Zr(OH)_4$ forms), carbonates, or bicarbonates.

In an exemplary embodiment, the coprecipitation can be carried out by preparing aqueous solutions containing the Ce precursor and the Zr precursor and then adding the solutions to a precipitator (specifically, a precipitator aqueous solution), and for effective formation of the mixed support, the coprecipitation can be carried out under stirring conditions. Here, in each of the Ce precursor solution and the Zr precursor solution, the concentration range of the metal precursor (Ce precursor and Zr precursor) may be adjustable in a range of for example about 0.2 to 6 M, specifically about 0.4 to 3 M, and more specifically about 0.8 to 1.5 M. Further, the feeding amount between the Ce precursor and the Zr precursor can be adjusted according to the ratio of Ce and Zr in the desired mixed support.

In an exemplary embodiment, the coprecipitation may occur by a reaction between a precursor solution and a basic solution, and thus the precursor solution may be added to the precipitator solution, or vice versa. For example, the coprecipitation may be carried out in a manner in which the metal precursor solution is added (specifically added dropwise) after the temperature of the precursor solution is raised.

The pH in the precipitation reaction may be maintained in a range of for example, about 8 to 12, and specifically about 9 to 11. Besides, the mixing time in the reaction medium is not limited to a particular range, but may be adjustable in a range of for example about 2 to 30 minutes, and specifically about 5 to 15 minutes. The temperature of the coprecipitation reaction is not particularly limited, but may be selected in a range of about 20 to 100° C., about 50 to 90° C., and more specifically about 60 to 80° C., and the coprecipitation reaction may be carried out under stirring.

Upon the completion of the coprecipitation reaction, aging may be optionally carried out for a predetermined time (for example about 12 to 36 hours, specifically about 15 to 30 hours, and more specifically about 20 to 25 hours) to facilitate crystallization.

The solid precipitate thus formed can be recovered (or collected) from the stock solution by typical separation techniques, such as filtering, settling, or centrifuging, and thereafter, the separated and recovered precipitate (for example, in a cake form) may be washed with for example water (specifically, deionized water).

As a next step, the precipitate can be calcined under an oxygen atmosphere (e.g., in the presence of air) with or without an intermediate drying process, so that a crystalline solid solution phase can be formed. In case of drying, the drying temperature may be selected in a range of for example about 25 to 150° C., specifically about 75 to 125° C., and more specifically about 95 to 110° C. In the calcination step, the temperature may be adjusted in a range of for example about 300 to 900° C., specifically about 400 to 800° C., and more specifically about 500 to 700° C. In addition, a crushing (or pulverizing) step of the dried cakes may be optionally performed, and here, the particle size of the resulting powders of the mixed-support may be about 300 μm or smaller and specifically about 200 μm or smaller, and may be calcined in the form of particles with a predetermined size or smaller using sieving.

The calcined product is substantially free of organic components, and has properties as a support in substantially a pure mixed oxide form.

According to an exemplary embodiment, the mixed oxide support (or mixed support) may have a specific (BET) surface area in a range of at least about 90 $m^2/g$, specifically about 95 to 200 $m^2/g$, and more specifically about 100 to 120 $m^2/g$.

Meanwhile, copper (Cu) may be loaded on the $Ce_xZr_{1-x}O_2$ support prepared as described above. Here, the loading of Cu may be carried out using a loading (supporting) techniques known in the art, such as impregnation, deposition, ion-exchange, and deposition-precipitation.

For this, a metal precursor solution containing a Cu precursor, specifically a Cu precursor, specifically the metal precursor solution is provided. A usable example of the Cu precursor may include a water-soluble copper salt, such as copper hydroxide phosphate, copper nitrate, copper sulfate, copper acetate, copper formate, copper (II) chloride, and copper iodide, of which one may be used alone or two or more may be used in combination. In an exemplary embodiment, the concentration of the Cu precursor in the solution may be selected in a range of about 0.1 to 2.1 M, specifically about 0.5 to 1.7 M, and more specifically about 1 to 1.2 M considering of the amount of Cu loaded in the desired final catalyst.

After the mixed support is impregnated with the Cu precursor solution as described above, drying is carried out at about 25 to 150° C., and specifically about 75 to 110° C. for about 4 to 24 hours, and specifically about 8 to 16 hours, and calcination is carried out at under conditions of a temperature of about 300 to 800° C., and specifically about 350 to 500° C. and an oxygen atmosphere (for example, air). The calcination may be carried out for about 2 to 10 hours, specifically about 3 to 5 hours, and the ramping rate may be in a range of for example about 3 to 7° C./min, and specifically about 4 to 6° C./min.

As a result of the calcination step, CuO is loaded on the $Ce_xZr_{1-x}O_2$ support (i.e., $CuO/Ce_xZr_{1-x}O_2$), the specific surface area of which may be in a range of for example at least about 70 $m^2/g$, specifically about 75 to 150 $m^2/g$, and more specifically about 80 to 100 $m^2/g$.

Subsequently, a reduction step, for example a reduction treatment step by a reducing gas such as hydrogen and/or carbon monoxide, which may optionally contain an inert gas (e.g., $N_2$, He, Ar, etc.) as a dilute gas may be performed for catalyst activation. The reduction treatment may be performed at a temperature of about 180 to 320° C., specifically about 200 to 300° C., and more specifically about 220 to 280° C. The reduction treatment time is not particularly limited, but may be in a range of for example about 1 to 6 hours, and specifically about 2 to 5 hours. Through the reduction treatment as above, a catalyst represented by $Cu/Ce_xZr_{1-x}O_2$ can be produced.

Characterization of $Cu/Ce_xZr_{1-x}O_2$ Catalyst

In the $Cu/Ce_xZr_{1-x}O_2$ catalyst according to an embodiment of the present disclosure, the Cu content may be in a range of for example, about 0.5 to 20 wt %, specifically, about 1 to 15 wt %, and more specifically about 1 to 10 wt %, on the element basis. When the Cu content is less than a predetermined level or an excessively large amount, the yields of products may be decreased or the leaching of Cu may be caused by Cu agglomeration, and thus it may be advantageous to adjust the Cu content to the above-described range if possible. However, the above numerical range may be changed, depending upon the condensation conditions as below.

Meanwhile, in the $Cu/Ce_xZr_{1-x}O_2$ catalyst according to the present embodiment, the $Ce_xZr_{1-x}O_2$ support has a plurality of oxygen vacancies, and thus Cu can be loaded with a higher dispersion. Without being bound to a particular theory, the reason is supposed to be that a strong interaction occurs between the Cu species and the support surface, and the more base sites are formed by oxygen vacancies created when smaller $Zr^{4+}$ ions (ionic radius: 0.84 Å) are added to the $CeO_2$ lattice (ionic radii of $Ce^{4+}$ and $Ce^{3+}$: 0.97 Å and 1.10 Å).

In the present embodiment, oxygen vacancies are formed on the oxide surface due to the presence of more $Ce^{3+}$ on the ceria-rich $Ce_xZr_{1-x}O_2$ support, and the oxygen vacancies promote the formation of oxygen, and thus indicate increased oxygen storage capacity. Therefore, a quantitative level of oxygen vacancies in the support can be derived by measuring the oxygen storage capacity. On the basis of this correlation, the oxygen storage capacity indicating the amount of oxygen vacancies in the $Ce_xZr_{1-x}O_2$ support may be in a range of, for example about 500 to 1000 µmol/g, specifically about 600 to 900 µmol/g, and more specifically about 650 to 850 µmol/g.

Meanwhile, the amount of base sites in the $Cu/Ce_xZr_{1-x}O_2$ catalyst may be measured by carbon dioxide temperature programmed desorption ($CO_2$-TPD) analysis. This measurement technique is disclosed in detail in J. Phys. Chem., 91 (1987) 3310-3315, which is incorporated herein by reference. According to an exemplary embodiment, the amount of $CO_2$-TPD in the $Cu/Ce_xZr_{1-x}O_2$ catalyst may be in a range of about 50 to 600 µmol/g, specifically about 75 to 500 µmol/g, and more specifically about 100 to 400 µmol/g.

In addition, because of Cu loading with a high dispersion as described above, the $Cu/Ce_xZr_{1-x}O_2$ catalyst has desirable specific Cu surface area properties, and as a result, butanol, which is a reactant in the fermented product, can easily access to a catalytic site having a dehydrogenation function, specifically Cu particles (or clusters). For instance, as the content of ceria ($CeO_2$) in the mixed support increases, the Cu dispersion also increases, but when the content of ceria in the mixed support exceeds a predetermined level (for example, about 0.9), the Cu dispersion may rather decrease. In this regard, the specific Cu surface area may be measured by $N_2O$—RFC (reactive frontal chromatography). This specific surface area measurement technique is described in detail in the paper (Angew. Chem. Int. Ed., 53 (2014) 7043-7047), which is incorporated herein by reference.

In an embodiment, the specific Cu surface area in the $Cu/Ce_xZr_{1-x}O_2$ catalyst may be in a range of about 1 to 60 $m^2$/g, specifically about 5 to 50 $m^2$/g, and more specifically about 10 to 40 $m^2$/g. In addition, the size of Cu particles (or clusters) in the catalyst may be in a range of about 5 to 100 nm, specifically about 7 to 80 nm, and more specifically about 10 to 60 nm.

As such, it can be seen that the ceria-rich $Cu/Ce_xZr_{1-x}O_2$ catalyst shows an increased conversion of acetone and higher selectivities to aliphatic ketones. Furthermore, the ceria-rich $Cu/Ce_xZr_{1-x}O_2$ catalyst according to the present embodiment can suppress the leaching of Cu as much as possible even in the cross-aldol condensation reaction between acetone and butanol. In this regard, butyl aldehyde generated by dehydrogenation during the reaction between acetone and butanol may act as a cause of the leaching of Cu in the catalyst, but in the catalyst according to the present embodiment, a strong interaction is formed between the Cu metal and the $Ce_xZr_{1-x}O_2$ support, thereby suppressing the leaching of Cu as much as possible, leading to favorable stability. On the other hand, when a Ce oxide or Zr oxide support alone is used, the interaction between the Cu component and the oxide is lower than a required level, and thus the leaching of Cu is inevitable during a reaction.

Especially, it is noteworthy that the amount of oxygen vacancies (or oxygen storage capacity) and the amount of base sites can be adjusted through the change in Ce/(Ce+Zr) ratio in the mixed support.

Process for Producing Aliphatic Ketones from Fermented Product of Biomass

According to an embodiment of the present disclosure, a method for producing aliphatic ketones from a fermented product of biomass, specifically a fermented product containing acetone and butanol, is provided.

In an embodiment, the biomass used for fermentation may be typically starch, sugars, and the like, and specifically monosaccharides (glucose, fructose, galactose, xylose, arabinose, mannose, etc), disaccharides (sucrose, lactose, maltose, cellobiose, etc.), and other (oligo) saccharides, and may contain at least one of the above examples. For example, a cellulose-based biomass is composed of cellulose having β-1,4 linkages of glucoses, hemicellulose (arabinoxylan, galactomannan, and xyloglucan) having linkages of various pentoses and hexoses, and thus upon saccharification, hexoses, such as glucose, mannose and galactose, pentoses such as xylose and arabinose, and disaccharides such as cellobiose, may exist in a mixed state.

In this regard, an example of a microorganism producing butanol and the like through the fermentation of biomass may be typically microorganisms which belong to the genus *Clostridium*. The genus *Clostridium* microorganisms are gram-positive rod bacteria and anaerobic, and has a low GC content in chromosomal DNA and endospore-forming characteristics. In addition, the genus *Clostridium* is one of the largest taxa following the genus *Streptomyces*, and includes microorganisms having various characteristics, exemplified by pathogenic bacteria, butyric acid fermentation bacteria, butanol fermentation bacteria, and ethanol fermentation bacteria. Examples of the genus *Clostridium* microorganisms are known to be *Clostridium acetobutylicum*, *Clostridium beijerinckii*, *Clostridium saccharobutylicum*, *Clostridium saccharoperbutylacetonicum*, *Clostridium perfringens*, *Clostridium tetani*, *Clostridium difficile*, *Clostridium butyricum*, *Clostridium butylicum*, *Clostridium kluyveri*, *Clostridium tyrobutylicum*, and *Clostridium tyrobutyricum*. In this regard, examples of the *Clostridium* sp. usable in the present embodiment may be *Saccharolytic solventogenic Clostridium*, and specifically *Clostridium acetobutylicum*, *Clostridium beijerinckii*, *Clostridium saccharobutylicum*, *Clostridium butylicum*, and the like.

The fermentation process may be performed by preparing a biomass (specifically hydrocarbons, more specifically sugars) medium, inoculating the above-described microorganisms thereon, followed by incubation, and specifically, the fermentation process may be an acetone-butanol-ethanol (ABE) fermentation process. The fermentation process is an anaerobic fermentation process, by which acetone, butanol and ethanol are produced and iso-propanol and hydrogen are produced in small quantities. The ABE fermentation process is largely divided into two phases. In the early stage of growth, organic acids, such as acetic acid and butyric acid, are produced, and in the latter stage of growth, butanol and ethanol are produced. Here, acetic acid and butyric acid are absorbed into cells and used to produce ethanol and butanol, and acetone is produced during the reuse of the organic acids.

The fermentation may be carried out under conditions of pH of for example about 4.2 to 5 and a temperature of about 10 to 70° C. (specifically, about 20 to 60° C., and more specifically about 33 to 55° C.). In the early stage of fermentation, the solution may contain, for example, about 200 g/L or less, specifically 100 g/L or less of sugars, and optionally a nitrogen source. Here, ammonia may be used as a nitrogen source, which may be added for pH adjustment as pH decreases due to metabolic activity of microorganisms during the fermentation.

The fermented product is obtained through the above-described fermentation process of biomass, and the concentrations of butanol and acetone in the fermented product may be in ranges of for example about 15 to 50 g/L (specifically, about 20 to 35 g/L) and about 2 to 25 g/L (specifically about 10 to 20 g/L), respectively. In addition, the fermented product may further contain ethanol, and the concentration thereof may be in a range of for example 2 to 10 g/L (specifically about 3 to 6 g/L).

In an embodiment, the fermented product is used in the synthesis of aliphatic ketones, and here the above-described $Cu/Ce_xZr_{1-x}O_2$ catalysts may be used. For this, prior to the catalytic reaction, the fermented product may be subjected to a separation technique known in the art, for example, solvent extraction, pervaporation, adsorption, and the like alone or in combination, thereby separating a reactant including acetone and butanol (or acetone, butanol, and ethanol) therefrom, and this reactant may be used as a reactant or a starting material for the condensation reaction (specifically the dehydrogenative aldol condensation).

In an exemplary embodiment, an ester-based solvent, an alcohol-based solvent, an alkane-based solvent, an amine-based solvent, or the like may be used alone or in combination as an extraction solvent for solvent extraction of the fermented product. The fermented product is separated into an extractant phase and an aqueous phase by such solvent extraction, and then such aqueous phase (e.g., containing microorganism strains and parts of acetone, butanol and ethanol) in combination with biomass (specifically sugars) as a raw material may be transferred to the fermentation process. Meanwhile, the extractant phase is separated into a fraction containing acetone, butanol, and ethanol and an extraction solvent via distillation, and the separated fraction containing acetone and butanol (acetone, butanol, and ethanol) may be used as a reactant of the catalytic reaction. The separated extraction solvent may be recycled to the solvent extraction process of the prior step.

According to an exemplary embodiment, the separation process of the reactant for the catalytic reaction from the fermented product may be performed during or after the fermentation.

In the extraction during fermentation (commonly referred to as extractive fermentation), an extraction solvent is in direct contact with a fermentation aqueous solution, and at the fermentation operation temperature (commonly, room temperature to about 40° C.), the volume ratio of fermentation liquid:extraction solvent may be in a range of for example about 0.1 to 1:1, specifically about 0.25 to 0.9:1, and more specifically about 0.5 to 0.8:1.

The separation of the reactant for the catalytic reaction after the fermentation may be carried out using the above-mentioned extraction solvent under conditions of, for example, a temperature of room temperature to about 70° C. and a pressure of atmospheric pressure to about 100 bar.

Here, the volume ratio of fermentation liquid:extraction solvent may be in a range of for example about 0.1 to 1:1, specifically about 0.25 to 0.9:1, and more specifically about 0.5 to 0.8:1.

According to an exemplary embodiment, the molar ratio of acetone:butanol in the reactant or starting material may be in a range of for example about 0.1 to 2:1, specifically about 0.25 to 1.6:1, and more specifically about 0.4 to 1.2:1. According to another embodiment, the molar ratio of acetone:butanol:ethanol in the reactant or starting material may be in a range of for example about 0.1 to 10:about 2 to 10:1, specifically about 0.25 to 5:about 2.5 to 7:1, and more specifically about 0.5 to 2.5:about 3 to 5.5:1.

According to an embodiment, the above-described catalytic reaction may be accompanied by a dehydrogenation reaction represented by reaction scheme 1 and aldol-condensation reactions represented by reaction schemes 2 and 3 below.

$C_4H_9OH \rightarrow C_4H_8O + H_2$  [Reaction Scheme 1]

$C_4H_8O + C_3H_6O + H_2 \rightarrow C_7H_{14}O + H_2O$  [Reaction Scheme 1]

$C_7H_{14}O + C_4H_8O + H_2 \rightarrow C_{11}H_{22}O + H_2O$  [Reaction Scheme 3]

As described above, Cu in the $Cu/Ce_xZr_{1-x}O_2$ catalyst functions to produce butyl aldehyde by the dehydrogenation of butanol, and the $Ce_xZr_{1-x}O_2$ mixed support may act as an active component for the aldol condensation (cross-aldol condensation). In this connection, the amount of base sites varies depending on the ratio of $Ce/(Ce+Zr)$ in the mixed support, and the dispersion of Cu is controlled according to the amount of oxygen vacancies, so the dehydrogenation can be controlled. In addition, the durability of the catalyst is excellent thanks to the suppression of Cu leaching during the dehydrogenation and the aldol condensation, and thus the conversion and selectivity can be maintained at favorable levels even for an extended reaction time.

In an exemplary embodiment, the synthesis reaction of the aliphatic ketones can be carried out under a substantially inert atmosphere, and for example, helium (He), nitrogen ($N_2$), argon (Ar), and neon (Ne) can be supplied into a reactor. In addition, the condensation reaction (specifically, the dehydrogenation and the aldol-condensation) may be carried out under conditions of a temperature of for example about 160 to 300° C., specifically about 180 to 280° C., and more specifically about 200 to 260° C. and a pressure of about 1 to 100 bar, specifically about 10 to 50 bar, and more specifically about 15 to 30 bar.

The aliphatic ketones produced via the aldol condensation reaction may have 6 to 14, specifically 7 to 11 carbon atoms, which corresponds to a range of gasoline ($C_{4-12}$) or jet oil ($C_{9-16}$). The aliphatic ketones thus produced may be exemplified as shown in General Formula 1, and may be obtained in the form of a single compound or a mixture of two or more compounds.

[General Formula 1]

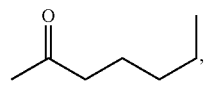
2-C7

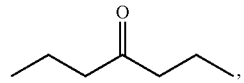
4-C7

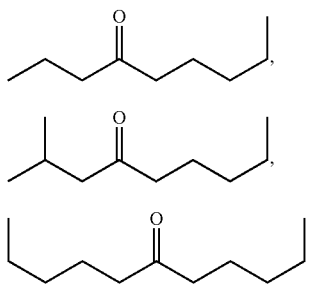

Meanwhile, the above-described synthesis of aliphatic ketones can be carried out in a batch or continuous mode. For the batch mode, the reaction time may be in a range of for example about 2 to 24 hours, specifically about 4 to 18 hours, and more specifically about 6 to 12 hours. For the continuous mode, the space velocity (WHSV) may be in a range of for example about 0.3 to 10 $hr^{-1}$, specifically about 0.5 to 5 $hr^{-1}$, and more specifically about 0.8 to 2 $hr^{-1}$.

In an exemplary embodiment, the conversion rate in the catalytic reaction may be for example at least about 60%, specifically at least about 65%, and more specifically at least about 75%, and the selectivity of the aliphatic ketones may be at least about 95%, specifically at least about 97%, and more specifically at least about 99%.

MODE FOR CARRYING OUT THE INVENTION

The present invention can be more clearly understood by the following examples, and these examples are merely illustrative of the present invention and are not intended to limit the scope of the invention.

EXAMPLES

In examples, sample analysis was performed according to the following procedure.

PXRD Analysis

PXRD analysis was performed with a Bruker D8 Discover with GADDS diffractometer using Cu Kα as an irradiation source (40 kV and 40 mA). A sample (10 mg) was heated to 900° C. (ramping rate: 5° C./min) in an air flow (100 sccm) to obtain a TG profile in NETZSCH TG209F1.

Specific BET Surface Area Analysis

A sample (0.2 g) was pre-treated at 100° C. and vacuum under 1 hour vacuum, and then the specific surface area of the sample was measured at −196° C. using Micromeritics 3Flex.

XP Spectrum Analysis

XP spectra were collected in a Theta probe base 21 system (Thermo Fisher Scientific Co.) using monochromatic Al Kα irradiation (1486.6 eV) with step increment: 0.050 eV. A support sample was pre-treated at 95° C. under vacuum for 12 hours prior to measurement.

Raman Scattering Analysis

Raman scattering analysis was performed by a LabRam Aramis Micro Raman spectrometer (Horriba Jobin Yvon) using an argon ion laser (532 nm) with 0.5 mW excitation.

$CO_2$-TPD Analysis

In an aldol condensation reaction, the amount of base sites is mainly used as an activity indicator, for which temperature-programmed desorption ($CO_2$-TPD) analysis is performed. The $CO_2$-TPD analysis was performed using BEL-CAT-B (BEL JAPAN, Inc) coupled with a MS detector (BEL-Mass). In the present example, the $CO_2$-TPD analysis was performed on a $Ce_xZr_{1-x}O_2$ support and a $Cu/Ce_xZr_{1-x}O_2$ catalyst, respectively. Prior to $CO_2$ adsorption, a CuO/CZ(x) sample (50 mg) was reduced for 3 hours under conditions of an argon flow (50 sccm) containing 10% $H_2$ and 250° C., and cooled to 35° C. under the He atmosphere. The reduced catalyst was supplied with He containing 5% $CO_2$ at 35° C. for 30 minutes, purged with He for 2 hours, and then heated from 35° C. to 850° C. at a rate of 10° C./min in a flow of He (30 sccm), so that the $CO_2$-TPD experiment was initiated.

$H_2$-TPR Analysis $H_2$-TPR analysis was performed in Micromeritics AutoChem 2910, wherein a CuO/CZ(x) sample (50 mg) was pre-treated at 90° C. under He atmosphere, and heated to 400° C. at a rate of 5° C./min in an argon flow (50 sccm) containing 10% $H_2$.

Specific Cu Surface Area Measurement

The specific Cu surface area is used as an indicator for the dehydrogenation reaction of butanol, and thus $N_2O$—RFC experiment was performed in BELCAT-B to evaluate the specific Cu surface area. A CuO/CZ(x) sample (50 mg) was reduced under conditions of an argon flow (30 sccm) containing 10% $H_2$ and a temperature of 250° C., cooled at 40° C. under a $H_2$ atmosphere, and then supplied with He containing 1% $N_2O$ (5 sccm), and the released nitrogen (m/z=28) was measured by an MS detector (BEL-Mass). The specific Cu surface area was calculated on the basis of a reaction stoichiometric ratio between copper and oxygen (Cu/O=2) and a copper surface density of $1.46 \times 10^{19}$ Cu atom $m^2$.

Oxygen Storage Capacity Measurement

In order to evaluate the oxygen storage capacity ($N_{OSC}$) of a $Ce_xZr_{1-x}O_2$ support, an oxidation test was performed, which is similar to the report in T. B. Nguyen, J. P. Deloume, V. Perrichon, Appl. Catal. A 249 (2003) 273-284. Prior to the test, a CZ(x) sample was pre-treated at 500° C. under Ar atmosphere for 1 hour, and reduced in an argon flow containing 10% $H_2$ at 250° C. for 2 hours.

After cooled to 25° C., the reduced catalysts were supplied with an argon flow (5 sccm) containing 1% $H_2$ for 2 hours, resulting in irreversible oxygen chemisorption ($N_2O$—OC). Then, the samples were sufficiently purged by He, at 25° C., followed by $N_2O$-TPO test using He containing 1% $N_2O$, and here the samples were heated to 900° C. at a rate of 10° C./min). The $N_{OSC}$ value was calculated by the total amount of $N_2O$ consumed during the $N_2O$—OC and $N_2O$-TPO experiments.

Example 1

Preparation of $Ce_xZr_{1-x}O_2$ Mixed Supports by Coprecipitation $Ce_xZr_{1-x}O_2$ supports with Ce/(Ce+Zr) ratios of 1, 0.9, 0.8, 0.5, 0.2, and 0 were synthesized, respectively.

Aqueous precursor solutions were prepared by dissolving 13.29 g of $Ce(NO_3)_3 \cdot 6H_2O$ as a Ce precursor and 7.08 g of $ZrO(NO_3)_2 \cdot xH_2O$ as a Zr precursor in 50 mL of water (total concentration: 1.2 M). Separately, 7.2 g of NaOH was dissolved in 600 mL of water in a 1 L-glass vessel (0.3 M), and the temperature was set at 70° C.

When the set temperature was reached, the aqueous solutions containing the Ce precursor and the Zr precursor were added dropwise at 15 mL/min to the aqueous NaOH solution under vigorous stirring. After the completion of the addition, the generated suspension was aged at 70° C. for 24 hours, and then subjected to filtration, thereby collecting a precipitate. In order to remove $Na^+$ ions and $NO^{3-}$ ions remaining in the precipitate, the precipitate was repeatedly washed with deionized water. A solid in a white cake form thus obtained was dried in an oven at 105° C. for 12 hours, followed by pulverization and sieving, thereby obtaining a powder of less than 200 μm. Thereafter, the powder was calcined at 600° C. (ramping rate: 5° C./min) for 3 hours under an air atmosphere, thereby obtaining a $Ce_xZr_{1-x}O_2$ mixed support (CZ(x)) with a Ce/(Ce+Zr) ratio of 0.5.

The $Ce_xZr_{1-x}O_2$ mixed supports with different Ce/(Ce+Zr) ratios were prepared by the same method except that the amounts of $Ce(NO_3)_3.6H_2O$ and $ZrO(NO_3)_2.xH_2O$ added were varied.

Production of $Cu/Ce_xZr_{1-x}O_2$ Catalyst (Cu Content: 10 wt %)

A Cu precursor aqueous solution was prepared by completely dissolving 0.85 g of $Cu(NO)_2$—$H_2O$ in 2 mL of water. The Cu precursor aqueous solution was added to 2 g of the previously prepared $Ce_xZr_{1-x}O_2$ supports and homogeneously dispersed therein. Thereafter, the dispersion thus obtained was dried in an oven at 105° C. for 12 hours, and calcined at 400° C. (ramping rate: 5° C./min) in air for 3 hours, thereby obtaining CuO-loaded $Ce_xZr_1$—$O_2$ samples (CuO/CZ (x)). Then, the CuO/CZ(x) samples were reduced at 250° C. (ramping rate: 5° C./min) in a pure $H_2$ flow (100 sccm) for 3 hours, thereby obtaining Cu/CZ(x) as a final catalyst.

Catalyst Characterization

The physical and chemical properties of the $Ce_xZr_{1-x}O_2$ supports, $CuO/Ce_xZr_{1-x}O_2$ samples, and $Cu/Ce_xZr_{1-x}O_2$ catalysts measured by the above-described analysis methods are summarized in Table 1 below.

Specific Cu Surface Area Analysis Results

According to Table 1, the specific Cu surface area was 15.1 μmol $g^{-1}$ for a Ce/(Ce+Zr) ratio of 1, but the addition of a small amount of Zr (Zr: 10 mol %) into the support increased the specific Cu surface area to 35.3 $m^2$ $g^{-1}$. As the Zr content increased, the specific Cu surface area decreased to 24.3 $m^2$ $g^{-1}$ (Zr: 20 mol %), 10.7 $m^2$ $g^{-1}$ (Zr: 50 mol %), 9.0 $m^2$ $g^{-1}$ (Zr: 80 mol %), and 5.2 $m^2$ $g^1$ (Zr: 100 mol %).

Figure 3:
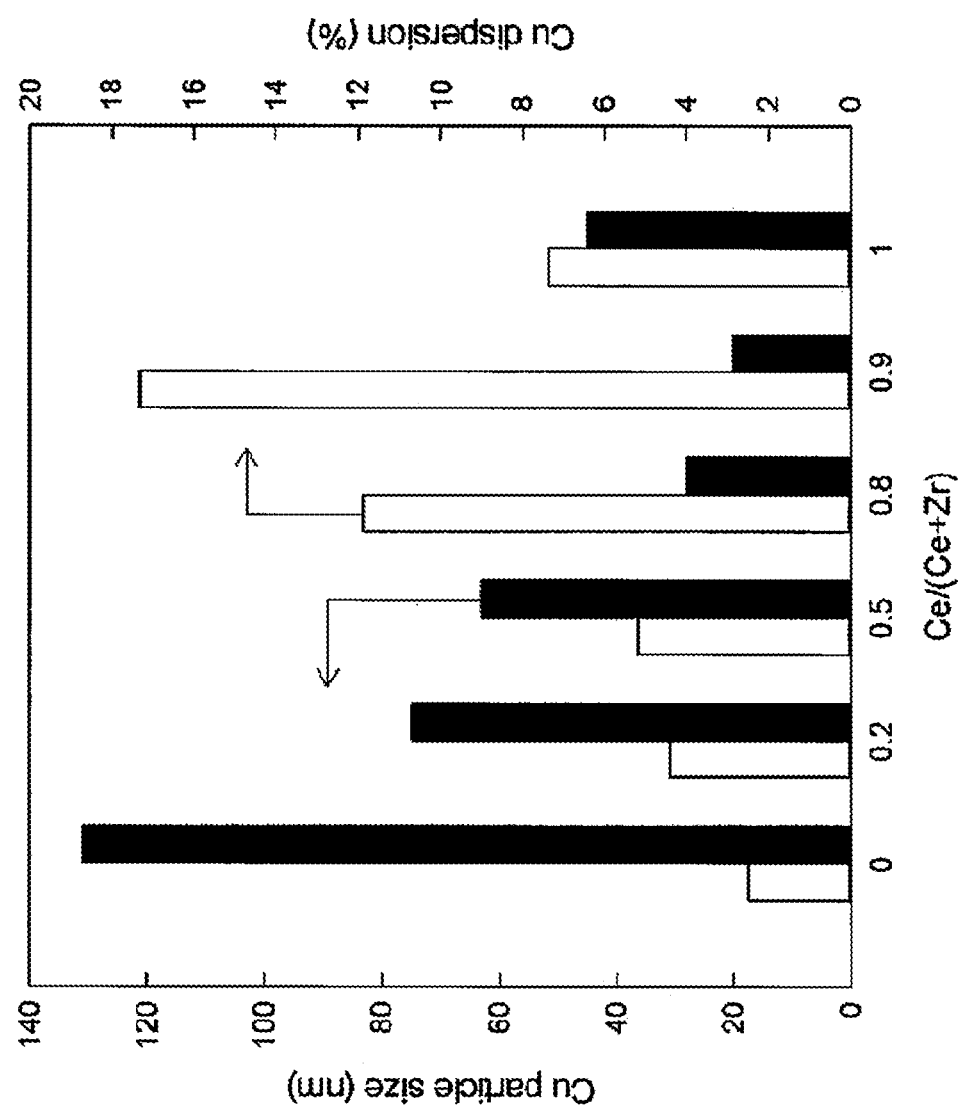
FIG. 3 is a graph showing the Cu particle size and Cu dispersion measured by $N_2O$—RFC experiment for $Cu/Ce_xZr_{1-x}O_2$ catalysts.
Figure 4:
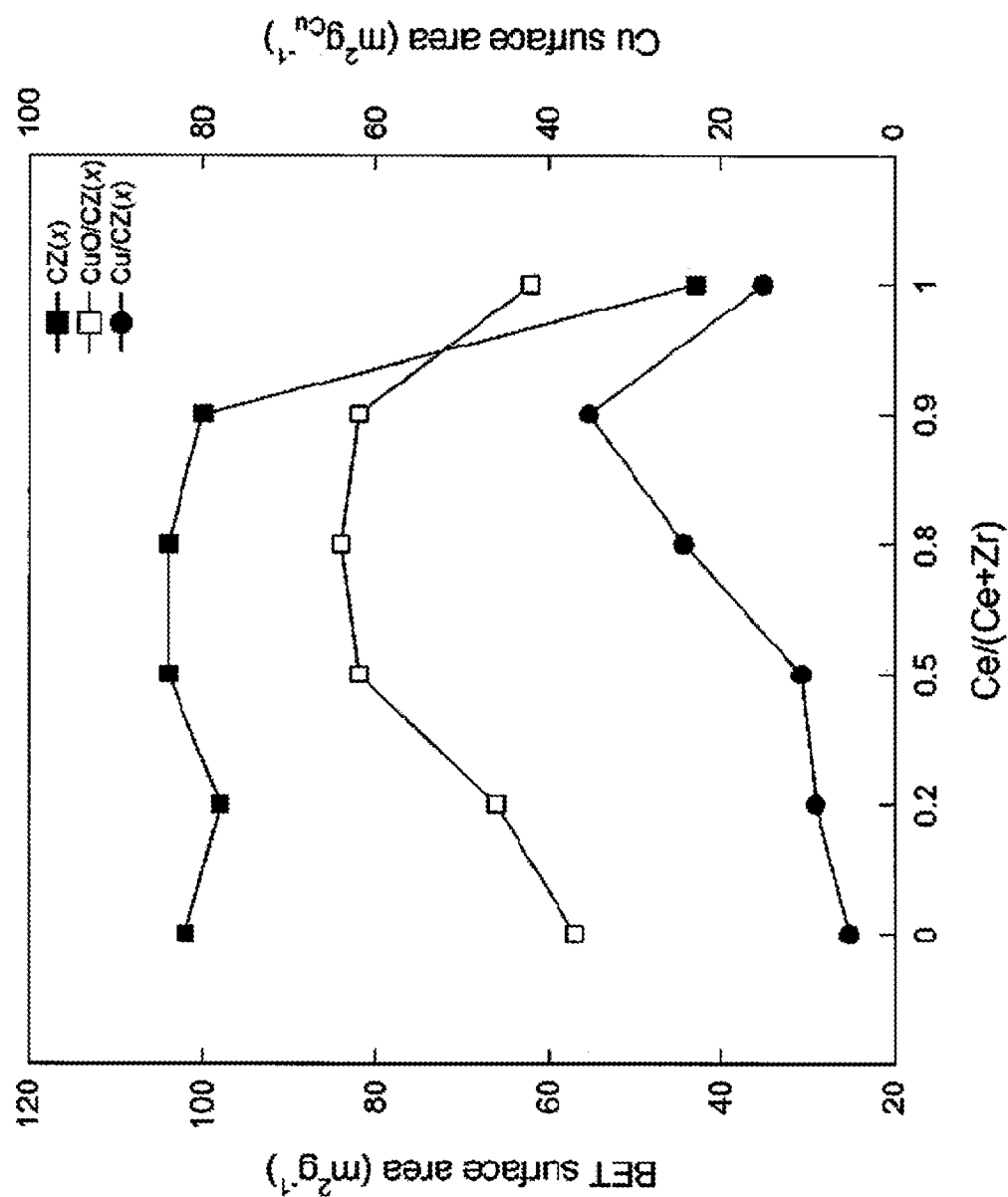
FIG. 4 is a graph showing specific BET surface areas of $Ce_xZr_{1-x}O_2$ supports and $CuO/Ce_xZr_{1-x}O_2$ catalyst samples as well as Cu surface areas of $Cu/Ce_xZr_{1-x}O_2$ catalysts.

FIG. 3 is a graph showing the Cu particle size and Cu dispersion measured by $N_2O$—RFC experiment on the $Cu/Ce_xZr_{1-x}O_2$ catalysts prepared in Example 1. In the drawing, as the $CeO_2$ content increases, the Cu dispersion increases from 2.5% for Cu/CZ(0) to 17.3% for Cu/CZ(0.9), and then decreases to 7.4% for Cu/CZ(1). The opposite trend was found for Cu particle size because smaller particles typically show higher fractions of exposed metal atoms in the surface. Thus, the Cu surface area shows a volcano-type relationship against the Ce/(Ce+Zr) ratio with a maximum value of 35.3 $m^2$ $g^{-1}$ at x=0.9.

Specific BET Surface Area Analysis Results

The $N_2O$—RFC analysis results may be associated with the specific surface area of unloaded $Ce_xZr_{1-x}O_2$ supports since the Cu loading measured by ICP-AES was close to 10 wt % within experimental errors for all the catalysts. Therefore, the specific BET surface areas ($S_{BET}$) of the CZ(x) and CuO/CZ(x) samples were measured, and the results are shown in FIG. 3. According to Table 1 and FIG. 3, all the CZ(x) supports showed similar $S_{BET}$ values in a range of 98 to 104 $m^2$ $g^{-1}$ except for 43 $m^2$ $g^{-1}$ for CZ(1), setting forth that $S_{CU}$ of the Cu/CZ(x) catalysts does not directly depend on $S_{BET}$ of the corresponding CZ(x) supports. These results are partially consistent with the surface area results of the

TABLE 1

| | CZ(x) | | | | CuO/CZ(x) | | Cu/CZ(x) | |
|---|---|---|---|---|---|---|---|---|
| | $S_{BET}$ ($m^2$ $g^{-1}$) | $D_p$ (nm) | $N_{CO2}$ (μmol $g^{-1}$) | $N_{OSC}$ (μmol $g^{-1}$) | $S_{BET}$ ($m^2$ $g^{-1}$) | $T_{r,max}$ (K) | $S_{Cu}$ ($m^2$ $g_{Cu}^{-1}$) | $N_{CO2}$ (μmol $g^{-1}$) |
| CZ(1) | 43 | 53.5 | 53.9 | 679.0 | 62 | 417/494 | 15.1 | 88.0 |
| CZ(0.9) | 100 | 39.2 | 100.5 | 813.5 | 82 | 406/458 | 35.3 | 313.4 |
| CZ(0.8) | 104 | 37.8 | 274.8 | 730.4 | 84 | 418/465 | 24.3 | 323.2 |
| CZ(0.5) | 104 | 35.6 | 109.4 | 691.2 | 82 | 443/486 | 10.7 | 196.5 |
| CZ(0.2) | 98 | 36.1 | 132.8 | 675.0 | 66 | 452/485 | 9.0 | 193.2 |
| CZ(0) | 102 | 39.2 | 66.0 | 493.6 | 57 | 485 | 5.2 | 99.3 |

PXRD Analysis Results

Figure 2A:
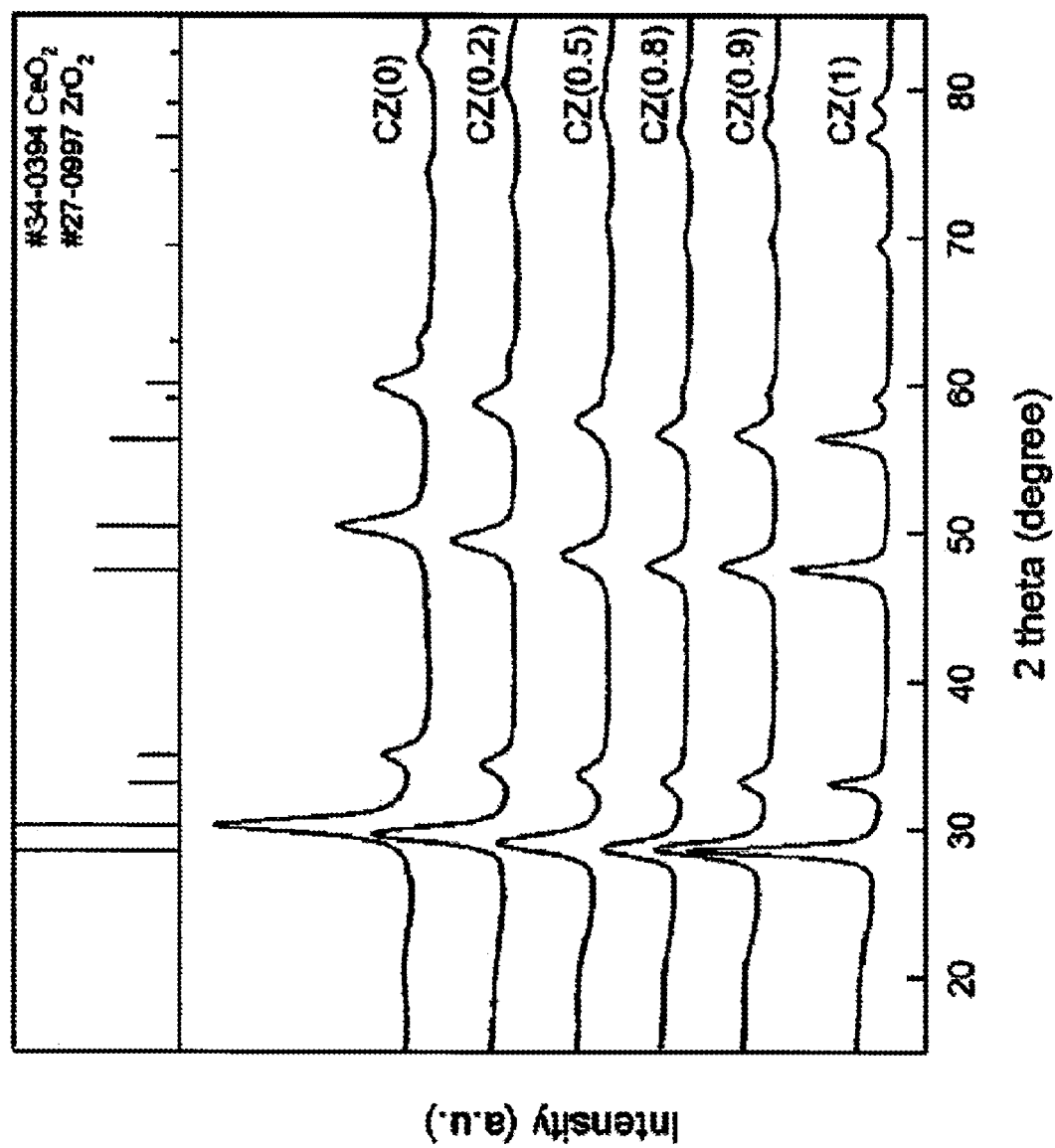
FIGS. 2a and 2b are PXRD patterns of (a) $Ce_xZr_{1-x}O_2$ supports and (b) $CuO/Ce_xZr_{1-x}O_2$ samples, respectively.
Figure 2B:
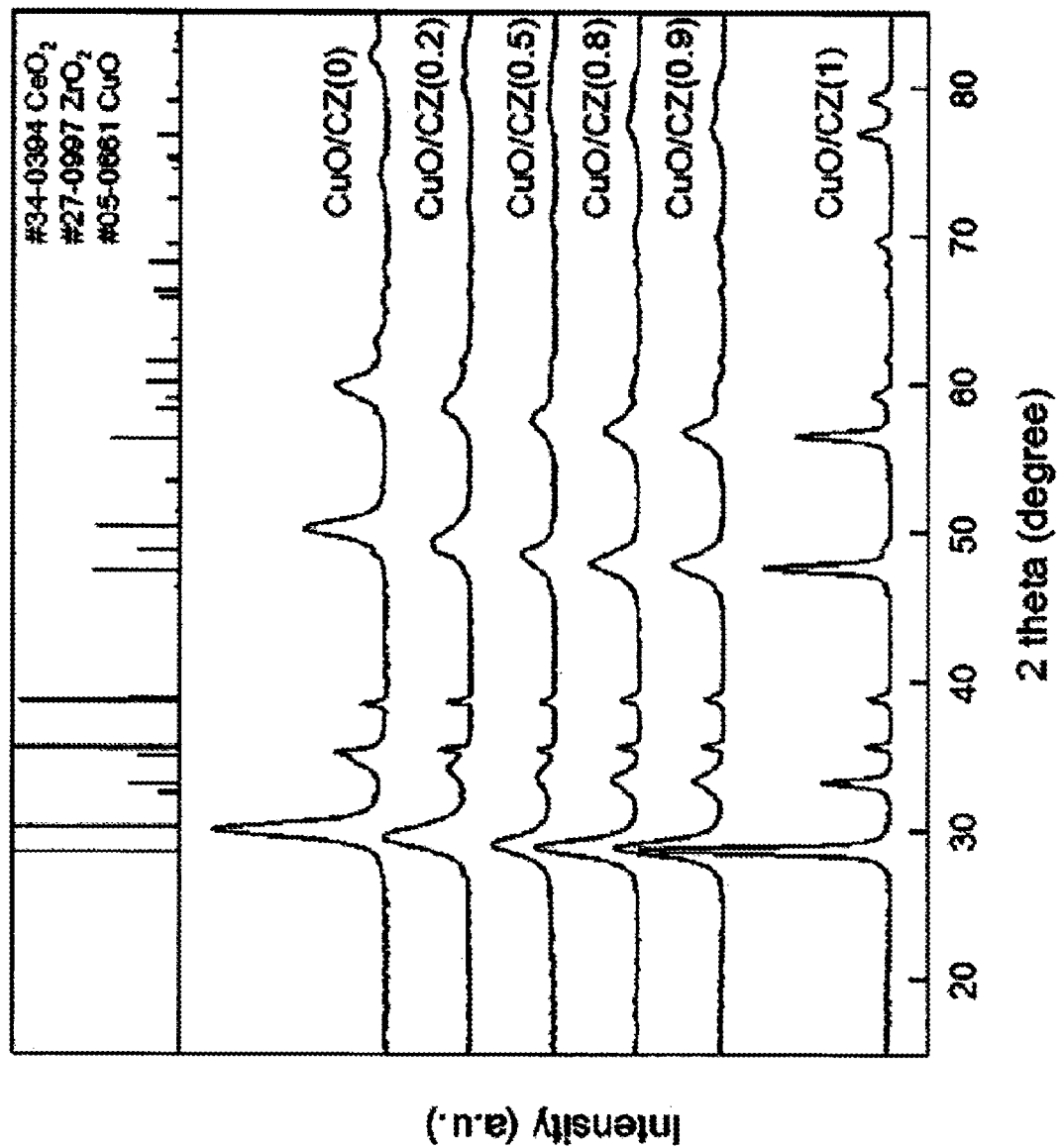

PXRD patterns of the $Ce_xZr_{1-x}O_2$ supports (CZ(x)) and $CuO/Ce_xZr_{1-x}O_2$ samples (CuO/CZ(x)) are shown in FIGS. 2a and 2b, respectively.

In FIG. 2a, CZ(1) and CZ(0) correspond to cubic ceria (JCPDS PDF #34-0394) and tetragonal zirconia (JCPDS PDF #27-0997), respectively. As the $ZrO_2$ content increases, the reflections of the $Ce_xZr_{1-x}O_2$ samples were shifted to high angles, indicating the transition from the cubic fluorite to the tetragonal structure. In addition, the reflections of the $Ce_xZr_{1-x}O_2$ samples were broadened due to small crystallite sizes, which is agreement with the results calculated by the Scherrer equation. Further, the symmetry of all reflections for CZ(x) with x=0.2, 0.5, 0.8, and 0.9 suggests the formation of single ceria-zirconia solid solution (no peak splitting by the homogeneous mixing of two phases).

According to FIG. 2b, the PXRD results shown in FIG. 2a were similar to those in the CuO/CZ(x) samples, indicating that Cu loading and subsequent calcination rarely change $Ce_xZr_{1-x}O_2$ structures. However, the CuO crystallite sizes for the CuO/CZ(x) samples could not be accurately calculated due to small reflections of CuO.

$CuO/Ce_xZr_{1-x}O_2$ samples wherein $S_{BET}$ of CuO/CZ(x) with x=0.5, 0.8, and 0.9 was similar to 83±1 $m^2$ $g^{-1}$. However, the low surface areas of CuO/CZ(x) with x=0 and 2 suggest that the interaction between the $Ce_xZr_1$—$O_2$ supports and the deposited Cu metal particles has an effect on $S_{BET}$ of CuO/CZ(x), and further Cu/CZ(x).

$CO_2$-TPD Analysis Results

Figure 5:
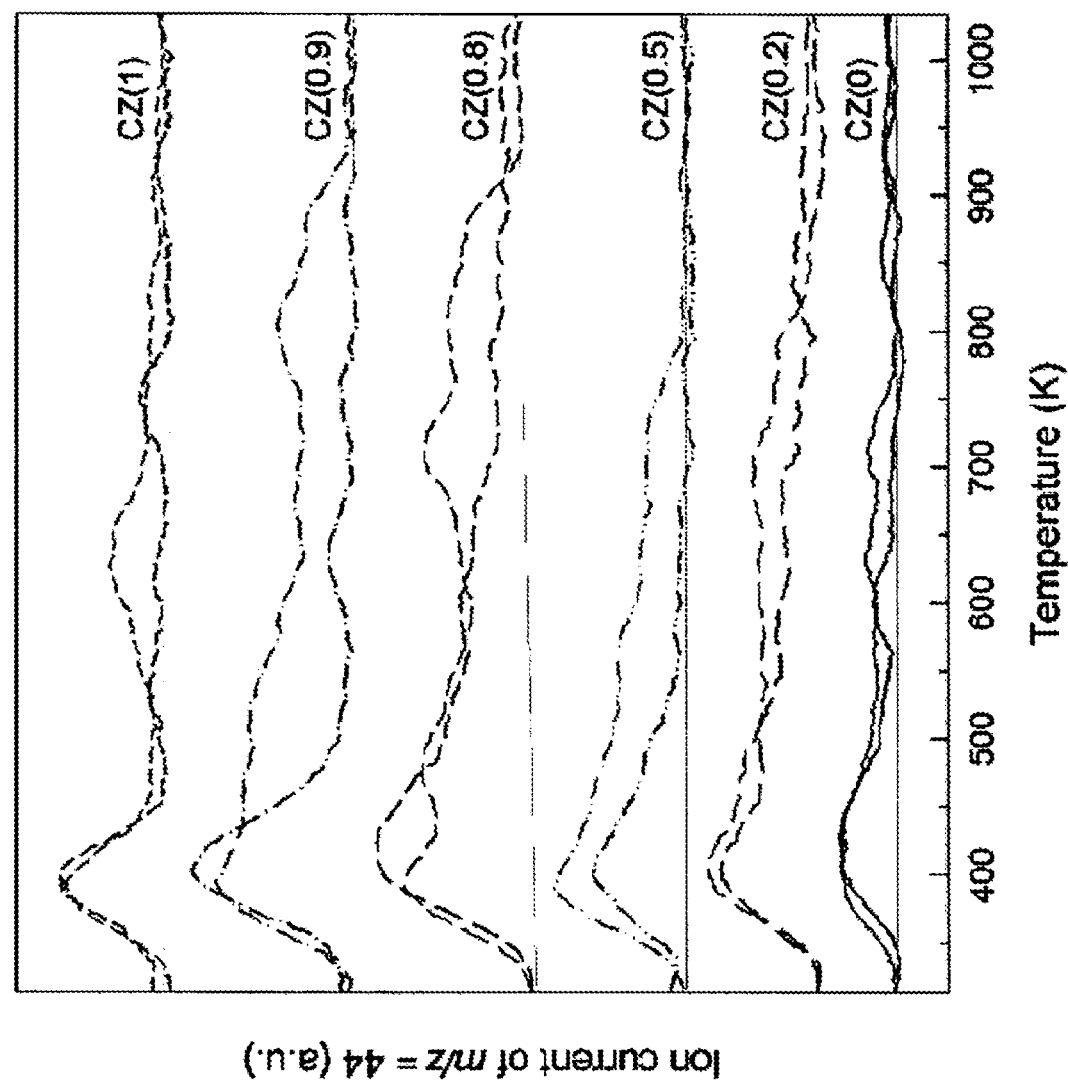
FIG. 5 is CO$_2$-TPD profiles of Ce$_x$Zr$_{1-x}$O$_2$ supports (black) and Cu/Ce$_x$Zr$_{1-x}$O$_2$ catalysts (red), where CO$_2$ (m/z=44) released from catalyst surface was detected using an MS detector)

The base site density and strength for the reduced Cu/CZ (x) catalysts was analyzed using $CO_2$-TPD experiment, and the results are shown in FIG. 5. The drawing shows the desorption profiles of $CO_2$ (m/z=44) detected using an MS detector.

Referring to Table 1, the Cu-unloaded $Ce_xZr_{1-x}O_2$ supports showed the highest value, 274.8 μmol $g^{-1}$, for x=0.8, and decreased values according to the x value, 132.8 μmol $g^{-1}$ (x=0.2), 109.4 μmol $g^{-1}$ (x=0.5), 100.5 μmol $g^{-1}$ (x=0.9), 66.0 μmol $g^{-1}$ (x=0), and 53.9 μmol $g^{-1}$ (x=1). The $Cu/Ce_xZr_1$—$O_2$ catalysts also showed the highest value, 323.2 μmol $g^{-1}$, for x=0.8, and 313.4 μmol $g^{-1}$ for x=0.9, showing a significantly higher value compared with the Cu-unloaded catalysts. The table above confirmed a reduction according to the x value, 196.5 μmol g$^{-1}$ (x=0.5), 193.2 μmol g$^{-1}$ (x=0.2), 99.3 μmol g$^{-1}$ (x=0), and 88.0 μmol g$^{-1}$ (x=1).

According to FIG. 5, all the catalysts have weak adsorption sites associated with surface OH group at 47 to 227° C. It was considered that the number of the weak adsorption sites is larger when Cu is supported on the mixed supports rather than the pure ceria (x=1) and zirconia (x=0) supports. According to a related document (J. I. Di Cosimo, C. R. Apesteguiia, M. J. L. Ginees, E. Iglesia, J. Catal. 190 (2000) 261-275, etc), the adsorption profiles at above 500 K (227° C.) may be divided into two regions for medium adsorption sites and strong adsorption sites associated with Mn$^+$—O$^{2-}$ pairs and low coordination O$^{2-}$ anions, respectively. It is interesting that the Cu/CZ(0.9) and Cu/CZ(0.8) catalysts retain lager numbers of medium and strong CO$_2$ binding sites than the other catalysts. As shown in Table 1, the total number of CO$_2$ binding sites (N$_{CO2}$) was also largest for the two ceria-rich catalysts (313.4 μmol g$^{-1}$ and 323.2 μmol g$^{-1}$). However, the amount of Cu loading is 10 wt %, relatively high, and the CO$_2$ adsorption can occur on the Cu clusters, and thus the contribution of Cu metal to CO$_2$ adsorption cannot be ignored.

Therefore, the base site density of the Ce$_x$Zr$_{1-x}$O$_2$ supports was measured using CO$_2$-TPD experiment after the hydrogen reduction treatment at 523 K (250° C.) Referring to Table 1, the total number of CO$_2$ binding sites in CZ(x) showed similar trends to those in Cu/CZ(x) as the Ce/Zr ratio changes although more CO$_2$ binding sites are available on Cu/CZ(x) due to surface Cu atoms loaded on the Ce$_x$Zr$_{1-x}$O$_2$ supports. Furthermore, the fact that Cu is responsible for medium and strong CO$_2$ binding sites of Cu/CZ(0.9) and Cu/CZ(0.8) catalysts may be explained by high amounts of accessible surface Cu atoms for the two catalysts (35.3 m$^2$ g$_{cu}^{-1}$ and 24.3 m$^2$ g$_{cu}^{-1}$, respectively).

Example 2

Synthesis of Aliphatic Ketones from Acetone and Butanol Using Cu/Ce$_x$Zr$_{1-x}$O$_2$ Catalysts A stainless batch reactor (entire volume: 150 mL) was fed with 11.26 g of acetone and 28.74 g of butanol, and charged with 0.5 g of an activated catalyst (Cu/Ce$_x$Zr$_{1-x}$O$_2$ catalyst), and then a reaction was initiated. The inside of the reactor was adjusted to 25 barg by the supply of N$_2$, which is inert gas, for 30 minutes in order to remove oxygen and moisture, followed by reaction at 240° C. (ramping rate: 10° C./min) for 6 hours. The product was collected, filtered through a syringe filter (diameter: 0.45 μm), and mixed with internal standard cyclohexane. The mixture was analyzed through Younglin YL6100 gas chromatography equipped with a flame ionized detector (FID) and HP-Innowax column (50 m, 0.2 mm, 0.4 μm).

The yield of product (3-hepten-2-one, 2-heptanone, 2-heptanol, and 6-undecanone) was calculated on the basis of the amount of baked acetone by using Equation 1.

Yield (mol %) of product(i)=(number of moles of product(i))/(number of moles of acetone consumed)×100    [Equation 1]

Figure 6:
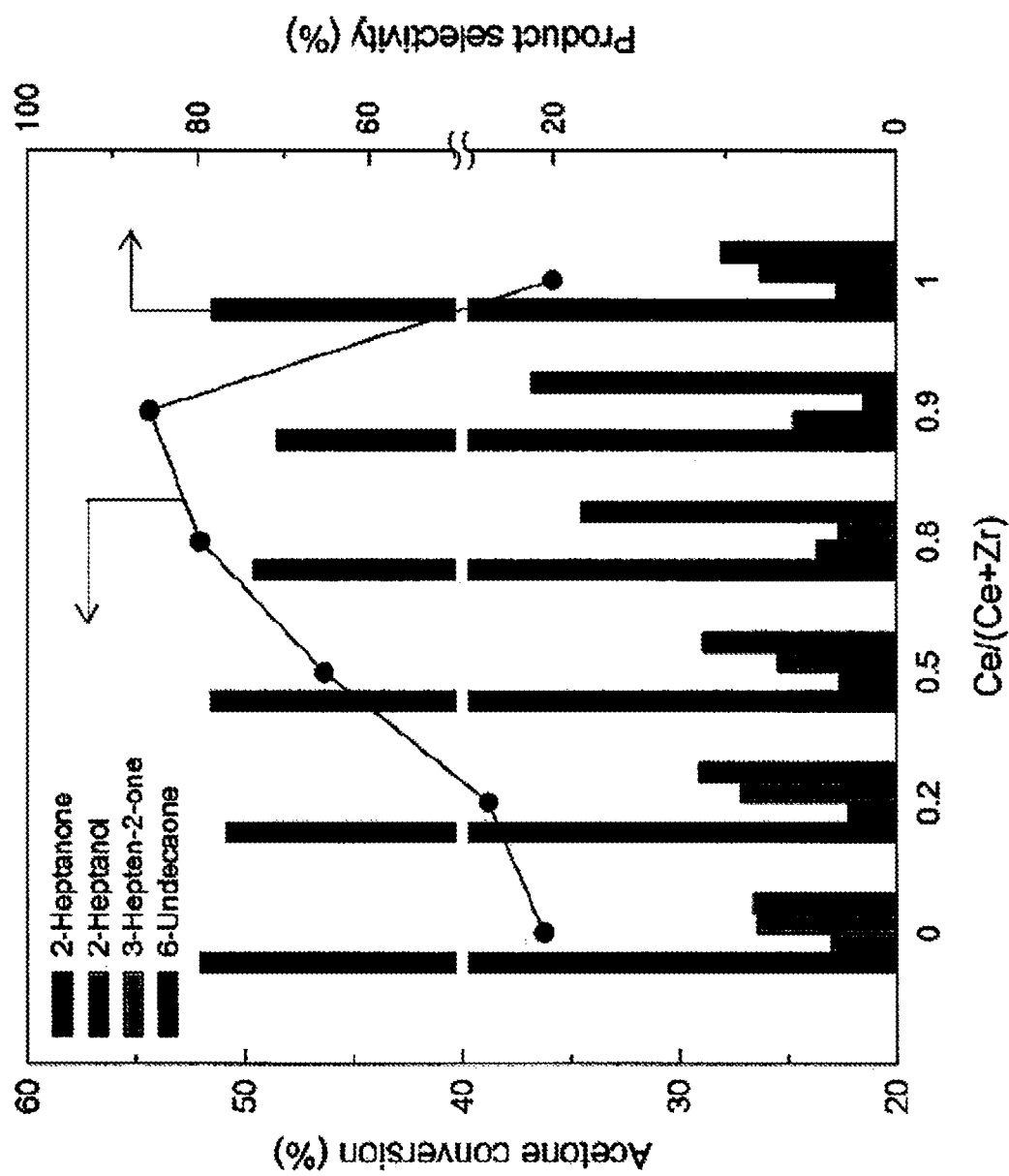
FIG. 6 is a graph showing acetone conversion and products selectivity over Cu/Ce$_x$Zr$_{1-x}$O$_2$ catalysts at 250° C.

The yield and selectivity of aliphatic ketones according to the x value in the Cu/Ce$_x$Zr$_{1-x}$O$_2$ catalysts are shown in Table 2 and FIG. 6.

TABLE 2

| | Metal content (mol %) | | Selectivity (%) | | Yield (%) |
|---|---|---|---|---|---|
| | Ce | Zr | 2-heptanone | 6-undecanone | |
| Cu/CZ (1) | 100 | 0 | 78.4 | 10.2 | 35.8 |
| Cu/CZ (0.9) | 90 | 10 | 70.8 | 21.3 | 54.4 |
| Cu/CZ (0.8) | 80 | 20 | 73.6 | 18.3 | 52.1 |
| Cu/CZ (0.5) | 50 | 50 | 78.5 | 11.3 | 46.3 |
| Cu/CZ (0.2) | 20 | 80 | 76.6 | 11.5 | 38.8 |
| Cu/CZ (0) | 0 | 100 | 79.8 | 8.3 | 36.2 |

According to the table above, the selectivity to 6-undecanone tended to increase as the content of Ce in the Ce$_x$Zr$_{1-x}$O$_2$ supports increased. The selectivity was 21.3%, the highest value, for x=0.9, and the selectivity decreased to 18.3% (x=0.8), 11.5% (x=0.2), and 11.3% (x=0.5) as the Ce content decreased. The ceria alone support (x=1) and the zirconia alone support (x=0) showed low selectivity, 10.2% and 8.3%, respectively. In this regard, the selectivity to 2-heptanone changed as the selectivity to 6-undecanone changed. This means that the selectivity to a desired product can be changed by the adjustment of the Ce/Zr ratio.

In addition, the acetone conversions by the Cu/CZ(1) catalyst and the Cu/CZ(0) catalyst are almost similar, 36±0.2%. The acetone conversion was increased to up to 54.4% as the x value increases from 0.2 to 0.9, meaning that higher catalytic activity is obtained for the ceria-rich Ce$_x$Zr$_{1-x}$O$_2$ supports.

Meanwhile, the main product for all the catalytic reactions was 2-heptanone, which is a mono-branched ketone produced by the condensation at a stoichiometric ratio of acetone and butanol with the same moles. As for the Cu/CZ(0.8) catalyst and Cu/CZ(0.9) catalyst, the selectivities to 2-heptanone were relatively low, 73.6% and 70.8%, respectively, but the selectivities to 6-undecanone were relatively high, 18.4% and 21.3%, respectively. These results are considered to be due to the fact that the high selectivity to 6-undecanone formed by di-branching of acetone with butanol can be achieved by more basic catalysts. Also, a high selectivity to 2-heptanol (6.0%; 2-heptanone hydrogenation product) and a low selectivity to 3-hepten-2-one (1.9%; aldol condensation product) for the Cu/CZ(0.9) catalyst are understood from the fact that the surface Cu atoms (S$_{CU}$) active for the hydrogenation reaction was highly available for this catalyst.

From these reaction results, high Cu dispersion and more basic sites can increase activity and selectivity to di-branched ketones of the Cu/CZ(0.9) catalyst.

In addition, the acetone conversion and the selectivity to 6-undecanone were Cu/CZ(0.2)<Cu/CZ(0.5)<Cu/CZ(0.8) <Cu/CZ(0.9), and this is associated with substitution of Ce ions by Zr$^{4+}$ ions in the mixed oxide of the support, leading to the mobility of O$^{2-}$ ions in the lattice.

Figure 7:
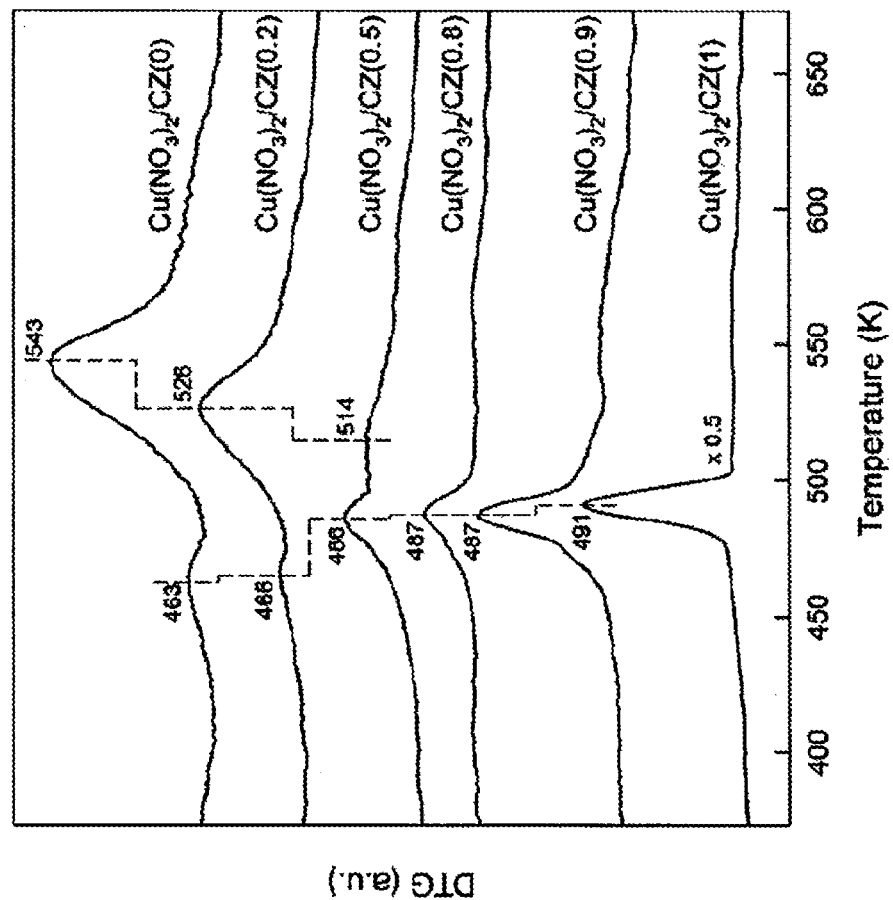
FIG. 7 is a graph showing DTG profiles of Cu(NO$_3$)$_2$-supported Ce$_x$Zr$_{1-x}$O$_2$ samples.

From this point of view, the thermal decomposition behaviors of the uncalcined Cu(NO$_3$)$_2$-impregnated Ce$_x$Zr$_{1-x}$O$_2$ samples were investigated. In general, the decomposition of bulk Cu(NO$_3$)$_2$ proceeds from 350 K (77° C.) to 523 K (250° C.), releasing H$_2$O and NO$_2$ simultaneously whereas that of the supported Cu(NO$_3$)$_2$ is shifted to lower temperatures. It is known that the support material has a significant effect on the decomposition process. FIG. 7 shows DTG profiles for Cu(NO$_3$)$_2$-supported Ce$_x$Zr$_{1-x}$O$_2$ samples.

According to the drawing above, Cu(NO$_3$)$_2$/CZ(1) showed a single sharp decomposition at 491 K (maximum decomposition temperature, $T_{d,max}$). Cu $(NO_3)_2$/CZ (0.9) and Cu$(NO_3)_2$/CZ(0.8) showed similar but less intense decomposition behaviors with slight shifts to 487 K. However, Cu$(NO_3)_2$/CZ(0.5) showed two decomposition peaks at $T_{d,max}$ of 486 K and 514 K. As the x value decreased from 0.5 to 0, the peak for the lower $T_{d,max}$ was less intense and the peak for the higher $T_{d,max}$ became larger with a shift to 543 K. These DTG results explain that the decomposition of the supported Cu$(NO_3)_2$ strongly depends on the ceria content in the mixed oxide.

Presumably, the decomposition found at low temperatures for the $Ce_xZr_{1-x}O_2$ supports with small amounts of $ZrO_2$ is associated with increased mobility of $O^{2-}$ ions in the $CeO_2$ lattice by substitution of Ce ions by $Zr^{4+}$ ions.

$H_2$-TPR Analysis Results

Figure 8:
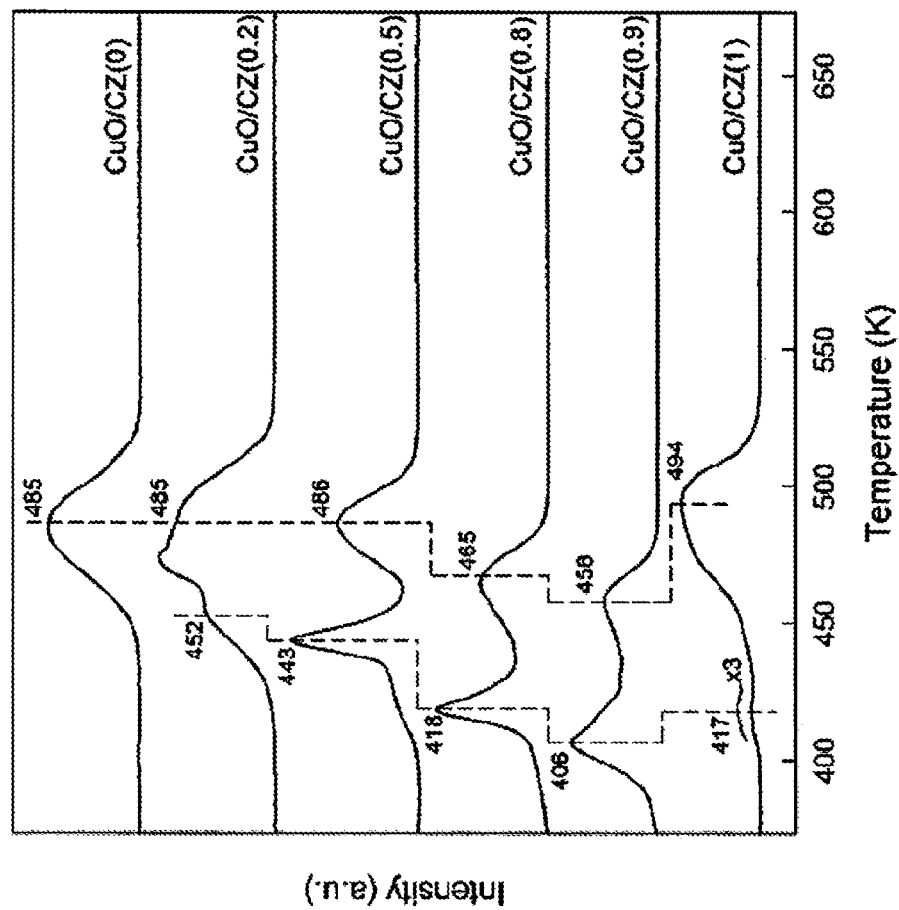
FIG. 8 is H$_2$-TPR profiles of CuO/Ce$_x$Zr$_{1-x}$O$_2$ samples.

The reduction characteristics of CuO/$Ce_xZr_{1-x}O_2$ samples were studied by $H_2$-TPR measurement because a strong effect of the metal-support interaction on reduction of the supported metal oxide particles is expected. In this regard, FIG. 8 shows $H_2$-TPR profiles of CuO/$Ce_xZr_{1-x}O_2$ samples. In this figure, CuO/CZ(0) exhibited a broad reduction peak with a maximum $(T_{r,max})$ at 485 K, while CuO/CZ(1) showed the similar peak at $T_{r,max}$ of 494 K together with a small hump at 417 K. The broad peak (corresponding to the direct reduction of bulk CuO crystallites into $Cu^0$) was split into two separate peaks ($T_{r,max1}$ and $T_{r,max2}$ for low- and high-temperature peaks) towards low temperatures for the CuO supported on the mixed oxides. As the x value increases from 0.2 to 0.9, the shift to low temperatures and the difference between $T_{r,max1}$ and $T_{r,max2}$ become larger. The peaks at $T_{r,max1}$ and $T_{r,max2}$ are ascribed to the reduction of highly dispersed CuO species strongly interacting with the support and the reduction of segregated CuO crystalline particles, respectively.

Also in FIG. 2b, the XRD results support the presence of segregated CuO due to the reflections of CuO at 35.5° and 38.8° observed for all the CuO/CZ(x) samples. In addition, the Cu dispersion measured by $N_2O$—RFC experiments shown in FIG. 3 is closely associated with the extent of $T_{r,max1}$ shift for the highly dispersed CuO species (i.e., the higher the Cu dispersion, the lower the $T_{r,max1}$). It is particularly noteworthy that the most significant shift of $T_{r,max1}$ was observed for CuO/CZ(0.9) with the highest Cu dispersion. Therefore, the TPR results suggest that $T_{r,max1}$ is affected by the strength of the interaction between supported CuO species and $Ce_xZr_{1-x}O_2$ surface.

Raman Spectrum Analysis Results

Figure 9:
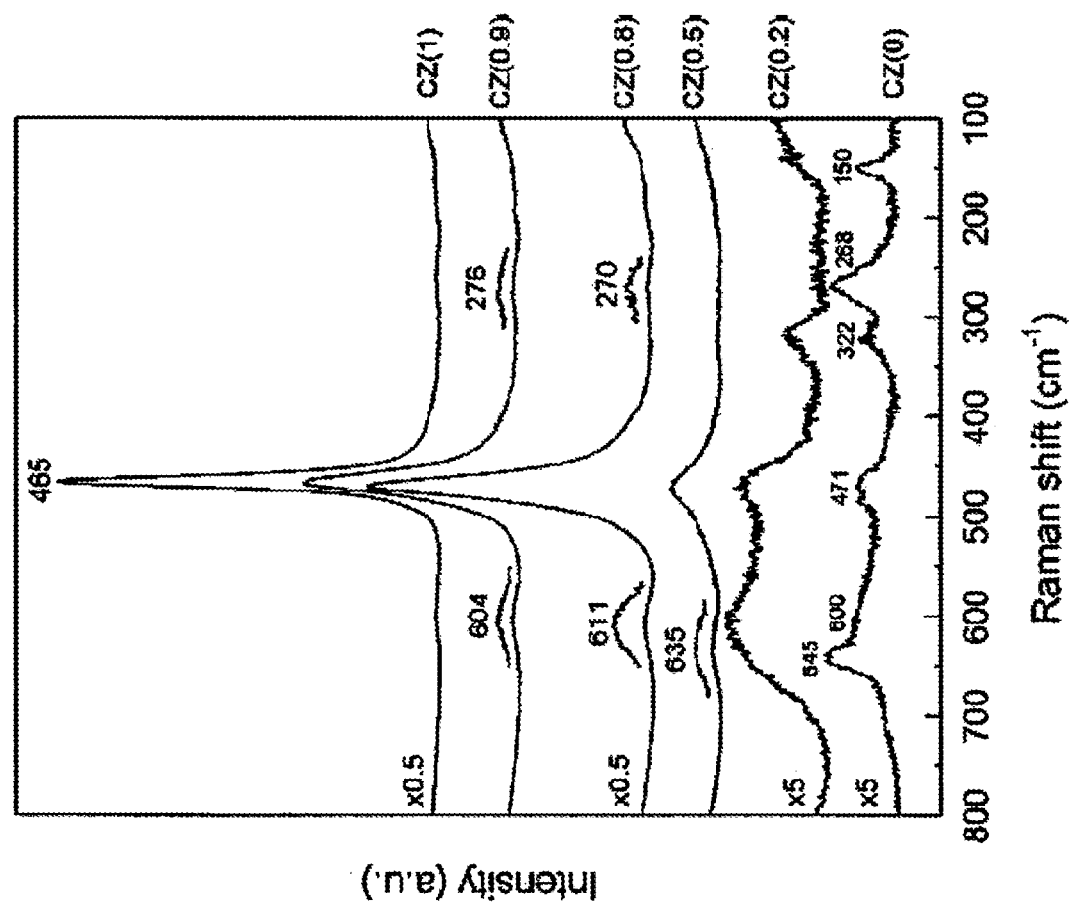
FIG. 9 is Raman spectra of Ce$_x$Zr$_{1-x}$O$_2$ supports.

Considering that the thermal decomposition of supported Cu$(NO_3)_2$ and the reduction of supported CuO strongly depend on the structure of the $Ce_xZr_{1-x}O_2$ supports, surface characteristics of the supports were investigated. The Raman spectra of $Ce_xZr_{1-x}O_2$ are shown in FIG. 9. According to this figure, pure $ZrO_2$ showed six Raman bands at 150, 266, 322, 471, 600, and 645 $cm^1$ theoretically predicted for tetragonal (t) zirconia, whereas the Raman band of pure $CeO_2$ was detected only at 465 $cm^{-1}$ due to the $F_{2g}$ vibration mode of the cubic fluorite type lattice.

The Raman spectrum of CZ(0.9) showed a $F_{2g}$ band at 465 $cm^1$ together with weak bands at 276 $cm^1$ and 604 $cm^{-1}$. The two additional bands are attributed to the tetragonal substitution of oxygen atoms from the ideal fluorite lattice position (276 $cm^{-1}$) and the nondegenerate longitudinal optical (LO) mode of ceria that is linked to oxygen vacancies in the ceria lattice (604 $cm^{-1}$). The band at 604 $cm^{-1}$ was blue shifted to 611 $cm^{-1}$ and 635 $cm^{-1}$ for CZ(0.8) and CZ(0.5), respectively. This is attributed to the formation of metastable pseudo-cubic (t") phase by t phase-like lattice distortions. The Raman bands for the ceria-rich $Ce_xZr_{1-x}O_2$ disappear for CZ(0.2) due to tetragonality of $ZrO_2$, which is supported by the XRD results in FIG. 2a, and is in agreement with the report that tetragonality of three tetragonal phases (t, t', and t") increased with the content of zirconia.

XP Spectrum Analysis Results

Figure 10:
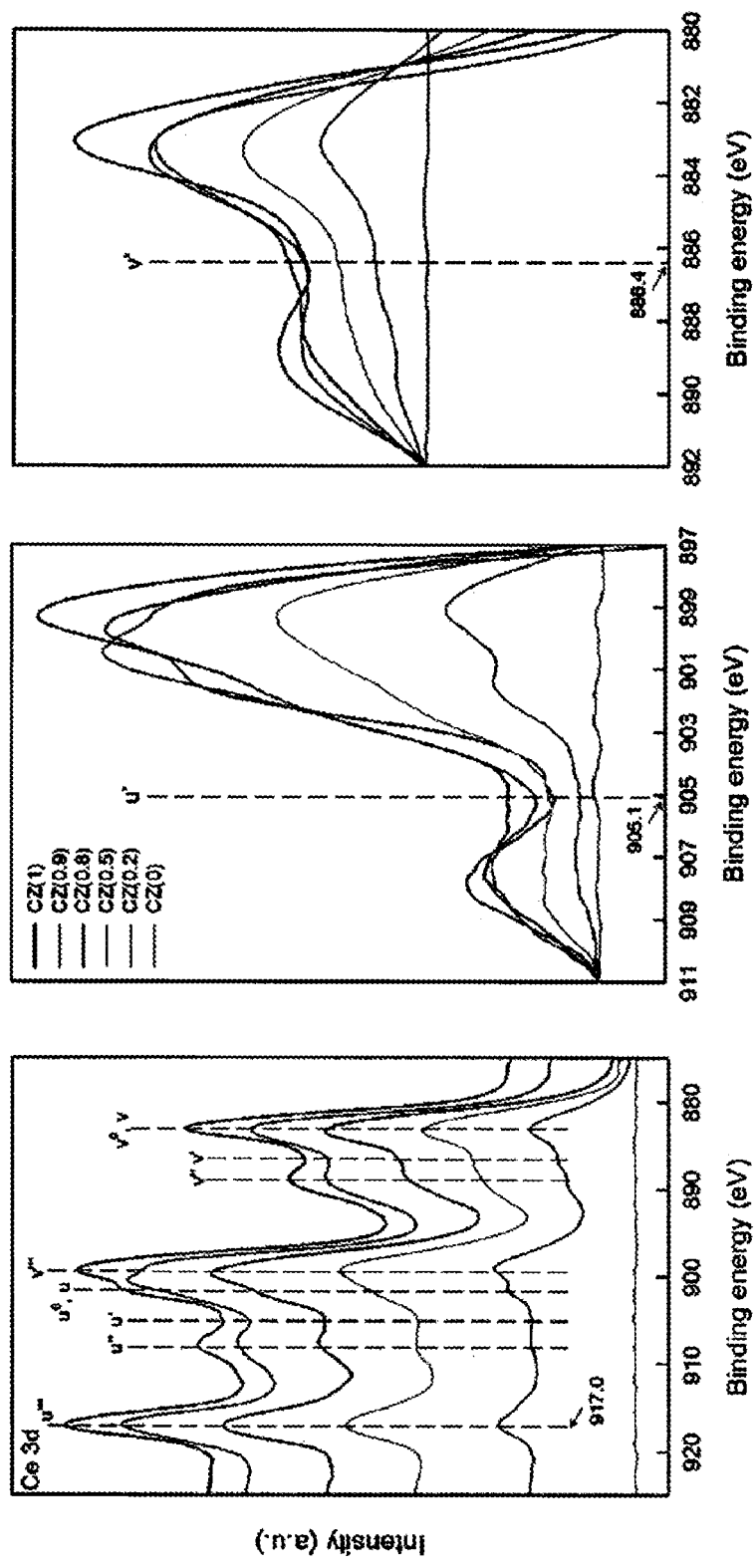
FIG. 10 is XPS Ce 3d spectra of Ce$_x$Zr$_{1-x}$O$_2$ supports in the range of 925-875 cm.

XPS analysis of $Ce_xZr_{1-x}O_2$ was performed to investigate the surface composition and the oxidation states of sample constituent atoms. In this regard, FIG. 10 shows XPS Ce 3d spectra of $Ce_xZr_{1-x}O_2$ supports in the range of 925-875 $cm^{-1}$. This figure shows complex Ce 3d spectra because the main Ce chemical valence of +4 coexists with a small amount of $Ce^{3+}$ on the surface of the $Ce_xZr_{1-x}O_2$ supports. The valence change of the Ce from +4 to +3 is attributed partly to the enhanced homogeneity of Ce and Zr atoms, and partly to spontaneous transformation of $Ce^{4+}$ (ionic radius: 0.97 Å) to larger $Ce^{3+}$ (ionic radius: 1.10 Å) resulting from substitution of $Ce^{4+}$ by $Zr^{4+}$ ions (ionic radius: 0.84 Å). In the right two diagrams in the figure (the intensity of spectra at 911 eV and 892 eV are identical for all samples), u' and v' lines are a little more intense for CZ(0.9) and CZ(0.8) than CZ(1) though more Ce atoms are present in pure ceria. This reveals that more $Ce^{3+}$ is present at the surface of the ceria-rich $Ce_xZr_{1-x}O_2$ supports.

Figure 11:
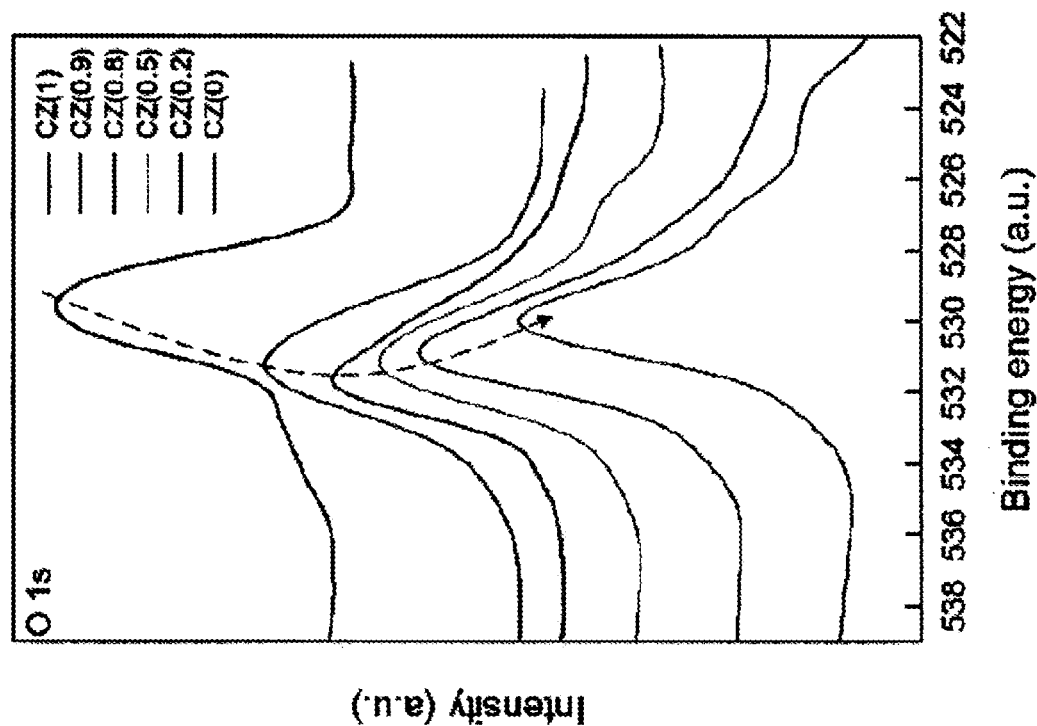
FIG. 11 is XPS O 1s spectra of Ce$_x$Zr$_{1-x}$O$_2$ supports.

The amplitudes of Zr $3d_{3/2}$ (184.3 eV) and Zr $3d_{5/2}$ (182.0 eV) lines just increased as a function of reducing Ce content. However, the XP spectra of the O 1s core level region showed an interesting feature as shown in FIG. 11. The O 1s binding energy (BE) depended on the Ce/Zr ratio, and decreased in the following order:

531.7 eV(CZ(0.8))>531.2 eV(CZ(0.9)) and CZ(0.5))>530.9 eV(CZ(0.2))>530.0 eV(CZ(0))>529.6 eV(CZ(1)).

When $Ce^{3+}$-related surface defects are formed, the additional O 1s BE indicates a shift of about 2 to 3 eV as compared with the O 1s BE of the stoichiometric $CeO_2$ surface at 530.1 eV (lattice oxygen atoms), and thus the O 1s shift to higher binding energies explains the formation of $Ce^{3+}$ at the surface. In addition, the O/(Ce+Zr) atom ratio was changed in a similar order: CZ(0.8)<CZ(0.9)<CZ(0.5) <CZ(1)<CZ(0.2)<CZ(0). These results should be due to the presence of more $Ce^{3+}$ on the ceria-rich $Ce_xZr_{1-x}O_2$ support, favoring the formation of oxygen vacancy in the oxide surface.

Oxygen Storage Capacity Analysis Results

Raman spectra and XPS analysis results revealed the presence of more $Ce^{3+}$ species in the ceria-rich $Ce_xZr_{1-x}O_2$ support. Because $Ce^{3+}$ favors formation of oxygen, the oxygen storage capacity ($N_{OSC}$) linked to oxygen vacancy was measured after the reduction of samples under the same conditions as in the catalyst pretreatment for the cross-aldol condensation reaction. The oxidation test using $N_2O$ gas consists of two steps: oxygen chemisorption at 25° C. and temperature-programmed oxidation to up to 900° C. The measured $N_{OSC}$ values are shown in Table 1 as described above. As the $CeO_2$ content increased, the $N_{OSC}$ value was 813.5 µmol $g^{-1}$, the highest value, for x=0.9, and as the x value changed, the $N_{OSC}$ value changed to 730.4 µmol $g^{-1}$ (x=0.8), 691.2 µmol $g^{-1}$ (x=0.5), 679.0 µmol $g^{-1}$ (x=1), 675.0 µmol g (x=0.2), and 493.6 µmol $g^{-1}$ (x=0). That is, the $N_{OSC}$ value increased from 493.6 µmol $g^{-1}$ for Cu/CZ(0) to 813.5 µmol $g^{-1}$ for Cu/CZ(0.9), and thereafter, decreased to 679.0 µmol $g^{-1}$ (x=1) for Cu/CZ(1).

Figure 12:
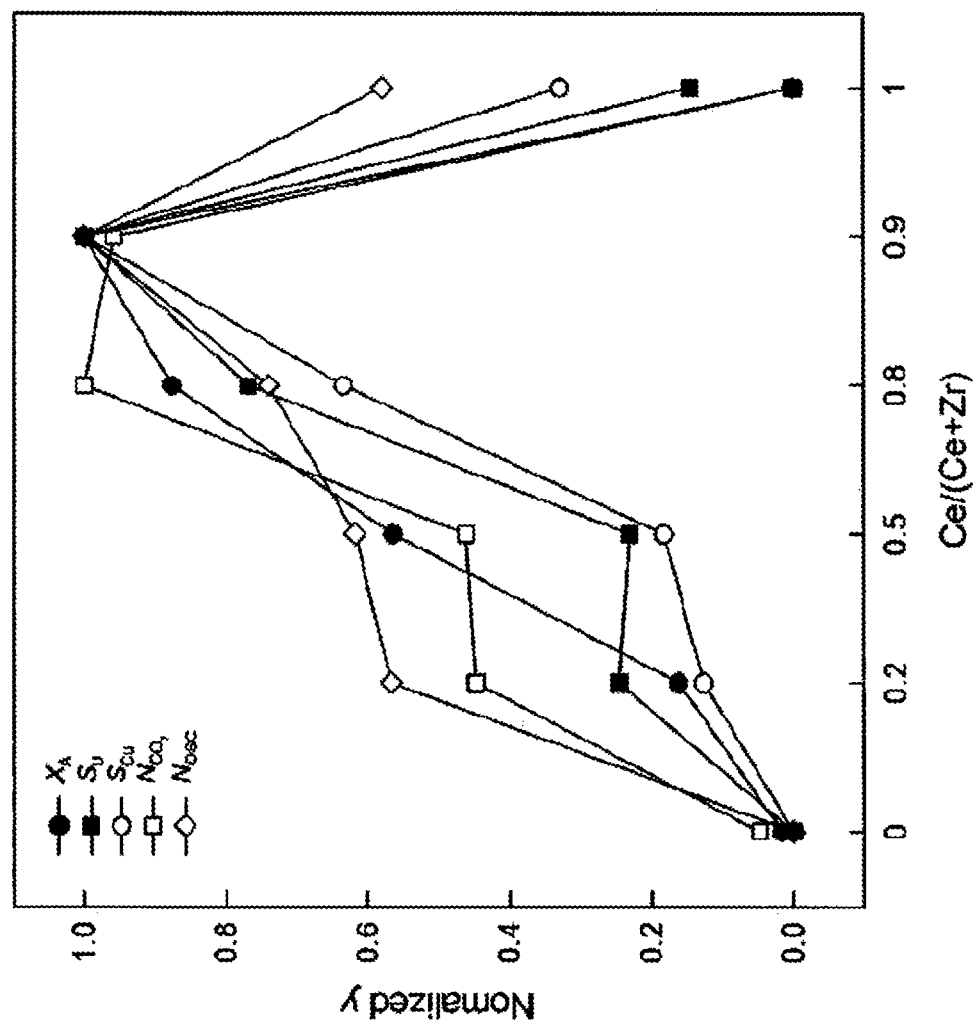
FIG. 12 is a correlation plot between the ceria content and the normalized properties (I$_y$) calculated by the equation I$_y$=[y−min(y)]/[max (y)−min(y)] (y=X$_A$, S$_U$, S$_{Cu}$, N$_{CO2}$, and N$_{OSC}$)

The oxygen storage capacity analysis results are similar to the quantitative results for catalytic activity and catalyst characteristics, and thus acetone conversion rate ($X_A$), selectivity to 6-undecanone ($S_U$), Cu surface area ($S_{Cu}$), $CO_2$ binding sites ($N_{CO2}$) r, and oxygen storage capacity ($N_{OSC}$)

were correlated with the Ce/(Ce+Zr) ratio, and the results are shown in FIG. 12. As shown in the figure, the dependences between each normalized parameter and the $CeO_2$ content were similar, and as for all the catalyst types of CZ (x), CuO/CZ(x), and Cu/CZ (x), the ceria-rich mixed oxide samples exhibited more enhanced effects than the zirconia-rich samples.

The cross-aldol condensation reaction is a two-step reaction in which butanol is first converted into butyl aldehyde through dehydrogenation and further condensed with acetone, affording 2-heptanone and 6-undecanone. Therefore, as $S_{Cu}$ (a catalyst property for butanol dehydration) and $N_{CO2}$ (a catalyst property for acetone-butyl aldehyde condensation) increased, the acetone conversion ($X_A$) and the selectivity to 6-undecanone ($S_U$) increased. This can be confirmed by comparing the variation of the related parameters shown in FIG. 12. The two activity descriptors $S_{Cu}$ and $N_{CO2}$ would be determined by the surface characteristics of the $Ce_xZr_{1-x}O_2$ supports, and thus $N_{CO2}$ are linked to oxygen vacancies in the mixed oxide lattice. As a consequence, the mixed oxide supports with more oxygen vacancies showed higher Cu dispersion due to the strong interaction between Cu species and the support surface, and also have more base sites are formed due to the oxygen vacancies created by the addition of smaller $Zr^{4+}$ ions to the $CeO_2$ lattice. This explains the enhanced conversion of acetone and higher selectivity to 6-undecanone for ceria-rich Cu/CZ(x) catalysts.

Figure 13:
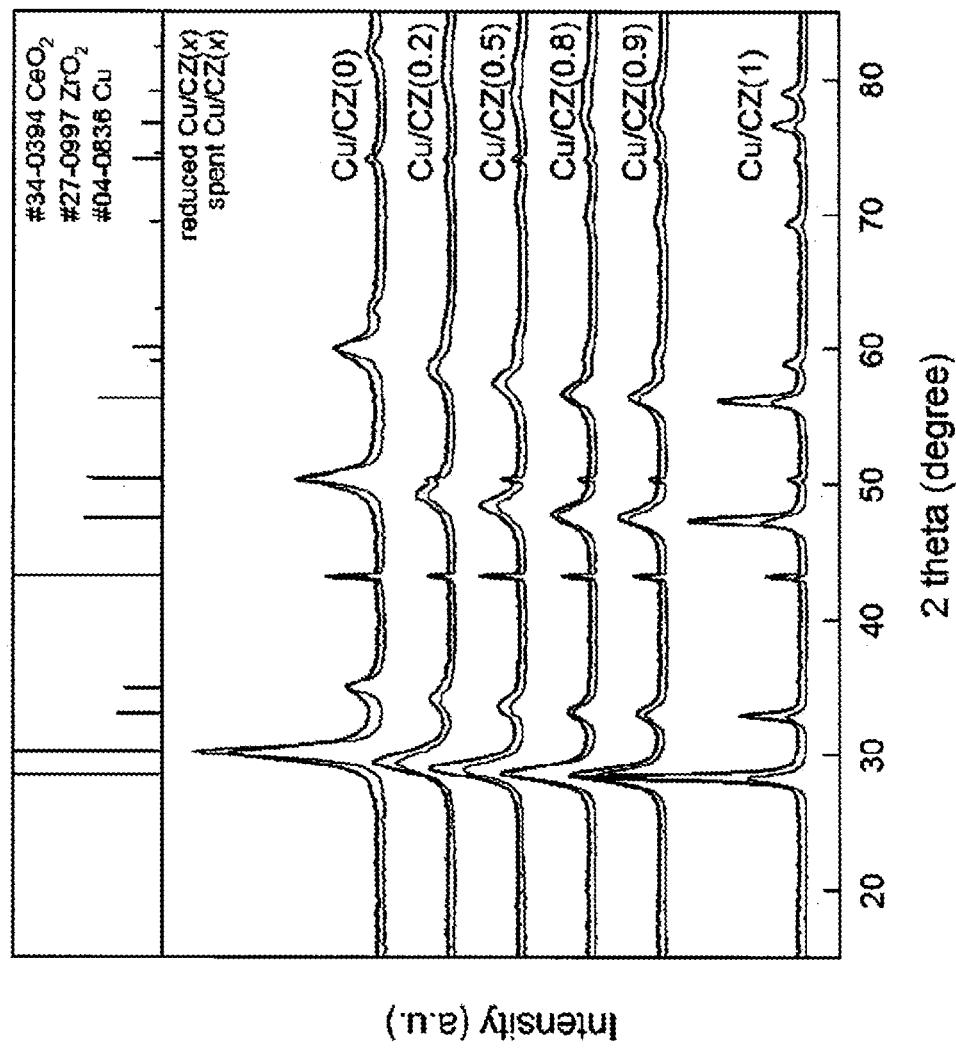
FIG. 13 is PXRD patterns of fresh Cu/Ce$_x$Zr$_{1-x}$O$_2$ catalysts (black) and spent Cu/Ce$_x$Zr$_{1-x}$O$_2$ catalysts (red).

Additionally, the stability of catalysts was evaluated by comparing the XRD patterns between novel $Cu/Ce_xZr_{1-x}O_2$ catalysts and spent $Cu/Ce_xZr_{1-x}O_2$ catalysts, and the results are shown in FIG. 13 (novel catalysts: black, used catalysts: red). Together, the catalysts produced by impregnating Cu into single metal oxide supports ($CeO_2$ and $ZrO_2$) were also investigated for the deformation after reaction.

As shown in the figure, the Cu/CZ(0.9) and Cu/CZ(0.8) catalysts showed the same reflections, indicating that the catalysts are stable under the reaction conditions. However, the other catalysts showed a decrease or an increase in the intensities of reflection of $Cu^0$ and $Ce_xZr_{1-x}O_2$ crystallites, resulting from the leaching by a reaction mixture or particle sintering. Therefore, it can be seen that the ceria-rich $Cu/Ce_xZr_{1-x}O_2$ catalysts had favorable durability in cross-aldol condensation of acetone and butanol. This stability is considered to be due to a strong interaction between $Cu^0$ and the $Ce_xZr_{1-x}O_2$ supports.

Considering the above-described results, it can be seen that favorable catalyst characteristics for cross-aldol condensation of bi-functional catalysts provided according to embodiments of the present disclosure can be obtained in the Cu-supported ceria-rich $Ce_xZr_{1-x}O_2$ supports rather than zirconia-rich catalysts and individual pure oxides-based supports.

Accordingly, simple modifications, additions and substitutions of the present invention should also be understood as falling within the scope of the present invention, without departing from the scope and spirit of the invention as disclosed in the accompanying claims.

The invention claimed is:

1. A method of producing a Cu/Ce—Zr-based catalyst for aldol condensation, the method comprising:
   a) preparing a mixed support represented by a general formula $Ce_xZr_{1-x}O_2$ (x is 0.5-0.95);
   b) loading a $Cu^{2+}$ precursor on the mixed support;
   c) converting the $Cu^{2+}$ precursor-loaded mixed support into its oxide form via calcination, and
   d) reducing the oxide obtained in step c) to produce a catalyst represented by $Cu/Ce_xZr_{1-x}O_2$, whereby CuO in the oxide is converted into its reduced form ($Cu^0$),
   wherein (i) the Cu content is 0.5 to 20 wt % on the element basis, (ii) the oxygen storage capacity is 500 to 1000 μmol/g, (iii) the specific Cu surface area is 1 to 60 $m^2/g$, and (iv) the amount of $CO_2$-TPD in the $Cu/Ce_xZr_{1-x}O_2$ catalyst is in a range of 100 to 600 μmol/g.

2. The method of claim 1, wherein the specific (BET) surface area of the mixed support prepared in step a) is at least 90 $m^2/g$ and the specific (BET) surface area of the oxide prepared in step c) is at least 70 $m^2/g$.

3. The method of claim 1, wherein the $Cu^{2+}$ precursor, as a water-soluble copper salt, is copper nitrate, copper sulfate, copper acetate, copper formate, copper (II) chloride, copper iodide, or a combination thereof.

4. The method of claim 1, wherein step a) comprises:
   a1) preparing precursor solutions for a support, the precursor solutions containing a Ce precursor and a Zr precursor;
   a2) forming a Ce—Zr composite precursor from the precursor solutions for a support; and
   a3) calcining the Ce—Zr composite precursor to form a mixed support in an oxide form.

5. The method of claim 4, wherein each of the Ce precursor and the Zr precursor is in the form of water-soluble metal salt.

6. The method of claim 5, wherein each of the Ce precursor and the Zr precursor is in the form of halide, hydroxide, nitrate, sulfate, oxalate, carbonate, acetate, ammonium nitrate salt, phosphate, a compound containing oxide of its corresponding metal element, or a combination thereof.

7. The method of claim 4, wherein step a2) is performed by coprecipitation.

8. The method of claim 1, wherein step b) is performed by impregnation, deposition, ion-exchange, or deposition-precipitation.

9. The method of claim 1, wherein step c) is performed under a temperature of 300 to 500° C. and an oxygen atmosphere for 2 to 10 hours.

10. The method of claim 1, wherein step d) is performed at a temperature of 180 to 320° C. using a reducing gas containing hydrogen and/or carbon monoxide, which optionally contains an inert gas.

11. A Cu/Ce—Zr-based catalyst for aldol condensation in which Cu particles or clusters are supported on a mixed support represented by $Ce_xZr_{1-x}O_2$ (x is 0.5-0.95), the Cu particles or clusters being a reduced form thereof ($Cu^0$),
   wherein (i) the Cu content is 0.5 to 20 wt % on the element basis, (ii) the oxygen storage capacity is 500 to 1000 μmol/g, (iii) the specific Cu surface area is 1 to 60 $m^2/g$, and (iv) the amount of $CO_2$-TPD in the $Cu/Ce_xZr_{1-x}O_2$, catalyst is in a range of 100 to 600 μmol/g.

12. The catalyst of claim 11, wherein the catalyst has a form in which Cu particles or clusters are dispersed on the $Ce_xZr_{1-x}O_2$ mixed support and the size of the Cu particles or clusters is in a range of 5 to 100 nm.

13. A method for producing aliphatic ketones from a fermented product of biomass, the method comprising:
   A) obtaining a fermented product of biomass containing acetone and butanol;

B) converting a reactant derived from the fermented product of biomass into aliphatic ketones via a condensation reaction using a Cu/Ce—Zr-based catalyst; and C) separating and recovering the aliphatic ketones from the reaction product, wherein in the Cu/Ce—Zr-based catalyst, Cu particles or clusters are supported on a mixed support represented by $Ce_xZr_{1-x}O_2$ (x is 0.5-0.95), the Cu particles or clusters are the reduced form thereof ($Cu^0$), and the Cu/Ce—Zr-based catalyst satisfies the following requirements (i) to (iv):

wherein (i) the Cu content is 0.5 to 20 wt % on the element basis, (ii) the oxygen storage capacity is 500 to 1000 µmol/g, (iii) the specific Cu surface area is 1 to 60 $m^2/g$, and (iv) the amount of $CO_2$-TPD in the $Cu/Ce_xZr_{1-x}O_2$, catalyst is in a range of 100 to 600 µmol/g.

14. The method of claim 13, further comprising, separating a reactant including acetone and butanol from the fermented product of biomass, wherein the separated reactant is provided as the reactant derived from the fermented product of biomass in step B).

15. The method of claim 14, wherein the molar ratio of acetone:butanol in the separated reactant is in a range of 0.1 to 2:1.

16. The method of claim 13, further comprising, separating a reactant including acetone, butanol, and ethanol from the fermented product of biomass, wherein the separated reactant is provided as the reactant derived from the fermented product of biomass in step B).

17. The method of claim 13, wherein step B) is performed under conditions of a temperature of 160 to 300° C. and a pressure of 1 to 100 bar.

18. The method of claim 13, wherein the aliphatic ketones have 6 to 14 carbon atoms.

* * * * *